(12) United States Patent
Leenders et al.

(10) Patent No.: US 9,988,449 B2
(45) Date of Patent: Jun. 5, 2018

(54) PLEXIN D1 AS A TARGET FOR TUMOR DIAGNOSIS AND THERAPY

(71) Applicant: Modiquest B.V., Oss (NL)

(72) Inventors: Wilhelmus Petrus Johannes Leenders, Nijmegen (NL); Ilse Roodink, Loenen (NL); Jozef Maria Hendrik Raats, Nijmegen (NL)

(73) Assignee: Modiquest B.V., Oss (NL)

( * ) Notice: Subject to any disclaimer, the term of this patent is extended or adjusted under 35 U.S.C. 154(b) by 144 days.

(21) Appl. No.: 15/210,676

(22) Filed: Jul. 14, 2016

(65) Prior Publication Data

US 2016/0311900 A1  Oct. 27, 2016

Related U.S. Application Data

(60) Division of application No. 13/541,296, filed on Jul. 3, 2012, now Pat. No. 9,422,358, which is a continuation of application No. 11/996,166, filed as application No. PCT/EP2006/007241 on Jul. 20, 2006, now abandoned.

(30) Foreign Application Priority Data

Jul. 21, 2005 (EP) ................... 05076675

(51) Int. Cl.
| | | |
|---|---|---|
| A61K 39/00 | (2006.01) | |
| C07K 16/28 | (2006.01) | |
| A61K 39/395 | (2006.01) | |
| C07K 14/705 | (2006.01) | |
| A61K 9/00 | (2006.01) | |
| A61K 51/10 | (2006.01) | |
| A61K 47/68 | (2017.01) | |

(52) U.S. Cl.
CPC .......... *C07K 16/28* (2013.01); *A61K 9/0019* (2013.01); *A61K 39/39558* (2013.01); *A61K 47/6803* (2017.08); *A61K 47/6817* (2017.08); *A61K 47/6849* (2017.08); *A61K 51/1018* (2013.01); *C07K 14/705* (2013.01); *C07K 2317/22* (2013.01); *C07K 2317/569* (2013.01)

(58) Field of Classification Search
None
See application file for complete search history.

(56) References Cited

U.S. PATENT DOCUMENTS

| 5,869,045 A | 2/1999 | Hellstrom et al. |
| 2004/0180002 A1 | 9/2004 | Young et al. |
| 2006/0127902 A1 | 6/2006 | Madden et al. |
| 2007/0054271 A1 | 3/2007 | Polyak et al. |
| 2008/0311567 A1 | 12/2008 | Bruckl et al. |

FOREIGN PATENT DOCUMENTS

| EP | 1679372 A1 | 7/2006 |
| WO | 0114420 A2 | 3/2001 |
| WO | 0190190 A2 | 11/2001 |
| WO | 2004037282 A1 | 5/2004 |

OTHER PUBLICATIONS

Marshall, Science, 1995, 269:1050-55.
Orkin et al., Report and Recommendation of the Panel to Assess the NIH Investment in Research on Gene Therapy, NIH, 1995.
Eck et al., Goodman & Gilmans The pharmacological Basis of Therapeutics, 1996, 9th Edition, Chapter 5, McGraw-W, NY.
Ross et al., Human Gene Therapy, 1996, 7:1781-90.
Verma et al., Nature, 1997, 389:239-42.
Demartis et al., Eur J Nucl Med, 2001; 28:534-39.
Rubanyi, Mol. Aspects Med., 2001, 22:113-42.
White et al., Annu Rev Med 52:125-45, 2001.
Borsi et al., Int J Cancer, 2002; 102-75-85.
Van Der Zwaag et al., Plexin-D1, a novel plexin family member, is expressed in vascular endothelium and the central nervous system during mouse embryogenesis, Developmental Dynamics, Wiley-L1SS, Inc., New York, NY, US, vol. 225, No. 3, Nov. 2002, pp. 336-43.
Juengst, British Medical Journal, 2003, 326:1410-11.
Santimaria et al., Clin Cancer Res., 2003, 9:571-79.
Roodink et al., Plexin D1 expression is induced on tumor vasculature and tumor cells: a novel target for diagnosis and therapy? Cancer Research, vol. 65, No. 18, Sep. 2005, pp. 8317-23.

*Primary Examiner* — Mark Halvorson
(74) *Attorney, Agent, or Firm* — Patent Law Works LLP

(57) ABSTRACT

The present invention relates to plexin D1 for use as a targetable protein in the treatment or diagnosis of disorders that involve expression of plexin D1. Diagnosis is suitably effected by detecting the presence of plexin D1 in the body or a bodily tissue or fluid, whereas treatment is effected by targeting plexin D1 for delivery of therapeutics to the site where treatment is needed. The invention further relates to the use of molecules that bind plexin D1, a nucleic acid encoding plexin D1 or a ligand of plexin D1 for the preparation of a therapeutical composition for the treatment or diagnosis of disorders that involve expression of plexin D1. The disorders comprise disorders in which plexin D1 is expressed on tumor cells, tumor blood vessels or activated macrophages.

3 Claims, 19 Drawing Sheets

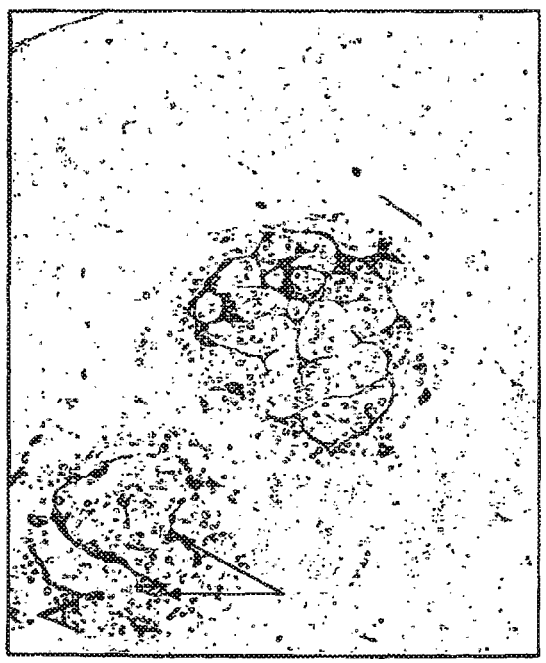
FIG. 2

SEQUENCE LISTING

<160> NUMBER OF SEQ ID NOS: 8

<210> SEQ ID NO 1
<211> LENGTH: 534
<212> TYPE: DNA
<213> ORGANISM: Artificial
<220> FEATURE:
<223> OTHER INFORMATION: Llama single domain antibody A12

<400> SEQUENCE: 1

| | | |
|---|---|---|
| atgaaatacc tattgcctac ggcagccgct ggattgttat tactcgcggc ccagccggcc | 60 |
| atggcccagg tgcagctgca ggagtctggg ggaggcttgg tgcagcctgg ggggtctctg | 120 |
| agactctcct gtgcagcctc tggaagcagt atcagtatca ataactgggg ctggtaccgc | 180 |
| caggctccag gaaaacagcg cgagcgggtc gcagctatat ctggtggtgg taaaacagtc | 240 |
| tatgcggact ccgtgaaggg ccgattcacc atctccagag acaacgccaa gaacacggtg | 300 |
| tatctgcaaa tgaacagcct gaaacctgag gatacggccg tctattactg tagagcagtc | 360 |
| cggaaaagta cgggttggct taggggggctt gacgtctggg gccaggggac ccaggtcacc | 420 |
| gtctccgcag aacccaagac accaaaacca caaccagcgg ccgcacatca tcaccatcat | 480 |
| caccatcatt atacagacat agagatgaac cgacttggaa agggggccgc atag | 534 |

<210> SEQ ID NO 2
<211> LENGTH: 177
<212> TYPE: PRT
<213> ORGANISM: Artificial
<220> FEATURE:
<223> OTHER INFORMATION: Llama single domain antibody A12

<400> SEQUENCE: 2

Met Lys Tyr Leu Leu Pro Thr Ala Ala Gly Leu Leu Leu Leu Ala
1               5                   10                  15

Ala Gln Pro Ala Met Ala Gln Val Gln Leu Gln Glu Ser Gly Gly Gly
            20                  25                  30

Leu Val Gln Pro Gly Gly Ser Leu Arg Leu Ser Cys Ala Ala Ser Gly
        35                  40                  45

Ser Ser Ile Ser Ile Asn Asn Trp Gly Trp Tyr Arg Gln Ala Pro Gly
    50                  55                  60

Lys Gln Arg Glu Arg Val Ala Ala Ile Ser Gly Gly Lys Thr Val
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Tyr Cys Arg Ala Val Arg Lys Ser Thr Gly Trp Leu Arg
        115                 120                 125

Gly Leu Asp Val Trp Gly Gln Gly Thr Gln Val Thr Val Ser Ala Glu
    130                 135                 140

Pro Lys Thr Pro Lys Pro Gln Pro Ala Ala Ala His His His His
145                 150                 155                 160

His His His Tyr Thr Asp Ile Glu Met Asn Arg Leu Gly Lys Gly Ala
                165                 170                 175

Ala

<210> SEQ ID NO 3
<211> LENGTH: 519
<212> TYPE: DNA

<213> ORGANISM: Artificial
<220> FEATURE:
<223> OTHER INFORMATION: Llama single domain antibody F8

<400> SEQUENCE: 3

```
atgaaatacc tattgcctac ggcagccgct ggattgttat tactcgcggc ccagccggcc      60
atggcccagg tgcagctgca ggagtctggg ggaggattgg tgcaggctgg agactctctg     120
agactctcct gtgcagcctc tggacgcacc ttcagtactt tgattatggc ctggttccgc     180
caggctccag gaaggagcg tgaatttgta gcggcgatta gccgggtgg cggtagcaca       240
agctatgcag actccgtgaa gggccgattc accatctcca gagacaattc aagaacgcg     300
gtgtatctac aaatgaacag cctgaaacct gatgacacgg ccgtctatta ctgtaatgcc     360
cggtacggta gccgaattta ctggggccag gggacccagg tcaccgtctc ctcagaaccc    420
aagacaccaa aaccacaacc agcggccgca catcatcacc atcatcacca tcattataca    480
gacatagaga tgaaccgact tggaaagggg gccgcatag                            519
```

<210> SEQ ID NO 4
<211> LENGTH: 172
<212> TYPE: PRT
<213> ORGANISM: Artificial
<220> FEATURE:
<223> OTHER INFORMATION: Llama single domain antibody F8

<400> SEQUENCE: 4

```
Met Lys Tyr Leu Leu Pro Thr Ala Ala Ala Gly Leu Leu Leu Leu Ala
 1               5                  10                  15
Ala Gln Pro Ala Met Ala Gln Val Gln Leu Gln Glu Ser Gly Gly Gly
             20                  25                  30
Leu Val Gln Ala Gly Asp Ser Leu Arg Leu Ser Cys Ala Ala Ser Gly
         35                  40                  45
Arg Thr Phe Ser Thr Leu Ile Met Ala Trp Phe Arg Gln Ala Pro Gly
     50                  55                  60
Lys Glu Arg Glu Phe Val Ala Ala Ile Ser Arg Gly Gly Gly Ser Thr
 65                  70                  75                  80
Ser Tyr Ala Asp Ser Val Lys Gly Arg Phe Thr Ile Ser Arg Asp Asn
                 85                  90                  95
Ser Lys Asn Ala Val Tyr Leu Gln Met Asn Ser Leu Lys Pro Asp Asp
            100                 105                 110
Thr Ala Val Tyr Tyr Cys Asn Ala Arg Tyr Gly Ser Arg Ile Tyr Trp
        115                 120                 125
Gly Gln Gly Thr Gln Val Thr Val Ser Ser Glu Pro Lys Thr Pro Lys
    130                 135                 140
Pro Gln Pro Ala Ala Ala His His His His His His His His Tyr Thr
145                 150                 155                 160
Asp Ile Glu Met Asn Arg Leu Gly Lys Gly Ala Ala
                165                 170
```

<210> SEQ ID NO 5
<211> LENGTH: 304
<212> TYPE: PRT
<213> ORGANISM: Artificial
<220> FEATURE:
<223> OTHER INFORMATION: Single chain antibody derived from anibody
       11F5H6

<400> SEQUENCE: 5

Met Lys Tyr Leu Leu Pro Thr Ala Ala Ala Gly Leu Leu Leu Leu Ala

```
            1               5                  10                 15
Ala Gln Pro Ala Met Ala Asp Tyr Lys Asp Ile Val Met Thr Gln Thr
                    20                  25                  30

Pro Leu Ser Leu Pro Val Ser Leu Gly Asp Gln Ala Ser Ile Ser Cys
                35                  40                  45

Arg Ser Ser Gln Ser Ile Val His Ser Asn Gly Asn Thr Tyr Leu Glu
             50                  55                  60

Trp Tyr Leu Gln Lys Pro Gly Gln Ser Pro Lys Leu Leu Ile Tyr Lys
 65                  70                  75                  80

Val Phe Asn Arg Leu Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
                100                 105                 110

Leu Gly Val Tyr Tyr Cys Phe Gln Gly Ser His Val Pro Leu Thr Phe
                115                 120                 125

Gly Ala Gly Thr Lys Leu Glu Leu Lys Arg Gly Gly Gly Gly Ser Gly
                130                 135                 140

Gly Gly Gly Ser Gly Gly Gly Arg Ala Pro Gly Gly Gly Gly Ser
145                 150                 155                 160

Glu Val Gln Leu Gln Gln Ser Gly Pro Glu Leu Val Lys Pro Gly Ala
                165                 170                 175

Ser Met Lys Ile Ser Cys Lys Ala Ser Gly Tyr Ser Phe Thr Gly Tyr
                180                 185                 190

Thr Met Asn Trp Val Lys Gln Ser His Gly Lys Asn Leu Glu Trp Ile
                195                 200                 205

Gly Leu Ile Asn Pro Tyr Asn Gly Gly Thr Ser Tyr Asn Gln Lys Phe
                210                 215                 220

Lys Gly Lys Ala Thr Leu Thr Val Asp Lys Ser Ser Ser Thr Ala Tyr
225                 230                 235                 240

Met Glu Leu Leu Ser Leu Thr Ser Glu Asp Ser Ala Val Tyr Tyr Cys
                245                 250                 255

Ala Arg Ala Ile Thr Thr Asp Gly Trp Phe Ala Tyr Trp Gly Gln Gly
                260                 265                 270

Thr Leu Val Thr Val Ser Ala Ala Ala Ala His His His His His His
                275                 280                 285

His His Tyr Thr Asp Ile Glu Met Asn Arg Leu Gly Lys Gly Ala Ala
                290                 295                 300

<210> SEQ ID NO 6
<211> LENGTH: 294
<212> TYPE: PRT
<213> ORGANISM: Artificial
<220> FEATURE:
<223> OTHER INFORMATION: Single chain antibody derived from antiboyd
      17E9C12

<400> SEQUENCE: 6

Met Lys Tyr Leu Leu Pro Thr Ala Ala Ala Gly Leu Leu Leu Leu Ala
 1               5                  10                  15

Ala Gln Pro Ala Met Ala Asp Tyr Lys Asp Ile Gln Met Thr Gln Thr
                20                  25                  30

Pro Ser Ser Leu Ala Val Ser Ala Gly Glu Lys Val Thr Met Ser Cys
                35                  40                  45

Lys Ser Ser Gln Ser Val Leu Tyr Ser Ser Asn Gln Lys Asn Tyr Leu
             50                  55                  60
```

```
Ala Trp Tyr Gln Gln Lys Pro Gly Gln Ser Pro Lys Leu Leu Ile Tyr
 65                  70                  75                  80

Trp Ala Ser Thr Arg Glu Ser Gly Val Pro Asp Arg Phe Thr Gly Ser
                 85                  90                  95

Gly Ser Gly Thr Asp Phe Thr Leu Thr Ile Ser Ser Val Gln Ala Glu
            100                 105                 110

Asp Leu Ala Val Tyr Tyr Cys His Gln Tyr Leu Ser Ser Trp Thr Phe
        115                 120                 125

Gly Gly Gly Thr Lys Leu Glu Ile Lys Arg Gly Gly Gly Gly Ser Gly
    130                 135                 140

Gly Gly Gly Ser Gly Gly Gly Ser Gly Gly Gly Ser Gln Val
145                 150                 155                 160

Gln Leu Gln Gln Ser Gly Ala Glu Leu Val Lys Pro Gly Ala Ser Val
                165                 170                 175

Lys Leu Ser Cys Thr Ala Ser Gly Phe Asn Ile Lys Asp Thr Tyr Met
                180                 185                 190

His Trp Val Lys Gln Arg Pro Glu Gln Gly Leu Glu Trp Ile Gly Arg
                195                 200                 205

Ile Asp Pro Ala Asn Gly Asn Thr Lys Tyr Asp Pro Lys Phe Gln Gly
210                 215                 220

Lys Ala Thr Ile Thr Ala Asp Thr Ser Ser Asn Thr Ala Tyr Leu Gln
225                 230                 235                 240

Leu Ser Ser Leu Thr Ser Glu Asp Thr Ala Val Tyr Tyr Cys Ala Met
                245                 250                 255

Asp Tyr Trp Gly Gln Gly Thr Ser Val Thr Val Ser Ser Ala Ala Ala
                260                 265                 270

His His His His His His His Tyr Thr Asp Ile Glu Met Asn Arg
                275                 280                 285

Leu Gly Lys Gly Ala Ala
    290

<210> SEQ ID NO 7
<211> LENGTH: 14
<212> TYPE: PRT
<213> ORGANISM: Artificial
<220> FEATURE:
<223> OTHER INFORMATION: Apoptosis inducing peptide

<400> SEQUENCE: 7

Lys Leu Ala Lys Leu Ala Lys Lys Leu Ala Lys Leu Ala Lys
1               5                   10

<210> SEQ ID NO 8
<211> LENGTH: 16
<212> TYPE: PRT
<213> ORGANISM: Homo Sapiens

<400> SEQUENCE: 8

Ala Leu Glu Ile Gln Arg Arg Phe Pro Ser Pro Thr Pro Thr Asn Cys
1               5                   10                  15
```

PLEXIN D1 AS A TARGET FOR TUMOR DIAGNOSIS AND THERAPY

CROSS-REFERENCE TO RELATED APPLICATION

This application is a divisional of U.S. patent application Ser. No. 13/541,296, filed Jul. 3, 2012, pending, which is a continuation of U.S. patent application Ser. No. 11/996,166, filed Mar. 3, 2008, abandoned, which is a national stage entry of International Patent Application Serial No. PCT/EP06/07241, filed Jul. 20, 2006, which published as PCT Publication No. WO 2007/009816 on Jan. 25, 2007, which claims benefit of European patent application Serial No. 05076675.7, filed Jul. 21, 2005, the disclosure of each of which is hereby incorporated herein in its entirety by this reference.

TECHNICAL FIELD

The present invention relates to the identification of a novel targetable protein that can be used in the treatment and diagnosis of tumors, in particular, solid tumors, and disorders that involve inflammation, in particular, rheumatoid arthritis, atherosclerosis and multiple sclerosis.

BACKGROUND

To grow beyond a size of 2-3 mm$^3$, tumors have to recruit a neovasculature via angiogenesis. Tumors accomplish this via expression of Vascular Endothelial Growth Factor-A (VEGF-A), either induced by hypoxia in the tumor center or as a result of malfunctioning tumor suppressor gene products or activated proto-oncogenes. A number of compounds that target the VEGF-A signaling pathway has been developed with the aim to inhibit angiogenesis and, consequently, tumor growth. Although such anti-angiogenic therapies have been effective in animal tumor models, translation to the clinical level has so far proven to be less successful (M. E. Eichhorn et al., *Drug Resist. Update* 7:125-138 (2004)).

For this, there is a number of possible explanations. In clinically relevant situations, tumors may have been growing for months or even years at the time of diagnosis, and a significant proportion of the vasculature may be more or less mature and thus insensitive to angiogenesis inhibition. This situation is in sharp contrast to that in most animal models in which, as a rule, aggressive, fast-growing tumors are studied. Furthermore, patients that are candidates for anti-angiogenic therapy are typically patients with disseminated, uncontrollable cancer and growth of metastases may not always be strictly dependent on angiogenesis. Because most metastases are blood-borne, they grow out in organs with intrinsically high vessel densities like liver, lung and brain, where they can grow in an angiogenesis-independent fashion by co-option of pre-existent vessels.

Indeed, an angiogenesis inhibitor that very effectively inhibits tumor growth in a number of subcutaneous tumor models (S. R. Wedge et al., *Cancer Res.* 62:4645-4655 (2002)) does not inhibit growth of infiltrative tumors in mouse brain. Moreover, upon treatment of mice carrying highly angiogenic brain tumors, angiogenesis inhibition did not result in a halt of further tumor progression, but rather in a progression after a phenotypic shift toward co-option and infiltration (W. P. Leenders et al., *Clin. Cancer Res.* 10:6222-6230 (2004)). These results imply that anti-angiogenic therapy should be supplemented by vascular targeting therapies in which the existing tumor vascular bed is attacked, resulting in secondary tumor cell death due to disruption of the tumor's blood supply.

To accomplish effective vascular targeting therapy, markers have to be identified that have specificity for tumor vasculature. Much effort has already been put in this, but with varying success. Effective vascular tumor targeting has been accomplished using single chain antibodies, directed against the fibronectin ED-B domain, which is selectively expressed and deposited in the extracellular matrix of newly formed vessels in angiogenic tumors (M. Santimaria et al., *Clin. Cancer Res.* 9:571-579 (2003)). Targeting of a $_v\beta_3$-integrin (the expression of which is restricted to immature vessels) using RGD peptides or Vitaxin yielded a disappointing result, whereas endoglin-expression was not specific for tumor blood vessels (J. A. Posey et al., *Cancer Biother. Radiopharm.* 16:125-132 (2001); E. Balza et al., *Int. J. Cancer* 94:579-585 (2001)).

In inflammatory diseases such as rheumatoid arthritis (RA) or atherosclerosis, angiogenesis and activation of the vasculature is also often part of the pathology. The vasculature here paves the way for inflammatory cells to extravasate and exert their destructive action. Such diseases can thus also benefit from targeting to blood vessels.

BRIEF SUMMARY

It is, therefore, the object of the present invention to provide a new targetable protein that can be used in the treatment and diagnosis of cancer and inflammatory diseases or diseases that involve inflammation.

In the research that led to the present invention, it was found that plexin D1 is expressed on the luminal side of endothelial cells in tumor blood vessels, on the tumor cells themselves and on activated macrophages that are found in tumors, in inflammation and in atherosclerotic plaques.

The invention thus relates to plexin D1 for use as a targetable protein in the treatment or diagnosis of disorders that involve expression of plexin D1.

The plexin family of receptors consists of four classes (PLXNA-D) and nine members in mammals. Plexins comprise a family of large, single-pass membrane proteins with homology to scatter factor receptors, encoded by the MET gene family. Members of the plexin family share Sema domains, Met-related sequences (MRS), a transmembrane region and intracellular motifs that are predictive of Rac/Rho-GTPase signaling (FIG. 1).

Since signaling via GTPases results in cytoskeletal rearrangements, events that are critically involved in formation of filopodia and lammelipodia and cellular migration, plexins can be regarded as regulators of migration.

Plexins are receptors for the semaphorins, a family of secreted, GPI-anchored or transmembrane proteins that is subdivided in seven subclasses. Each plexin has its own (set of) semaphorin binding partners, and each plexin-semaphorin combination results in a specific response. Class 3 semaphorins are potent axon repellants and are as such involved in morphogenesis of the nervous system (for review, see, R. J. Pasterkamp et al., *Curr. Opin. Neurobiol.* 13:79-89 (2003); H. Fujisawa, *J. Neurobiol.* 59:24-33 (2004)). For activation of plexins by the semaphorins, additional plexin binding partners may be required. These binding partners, neuropilin-1 and -2 (NP-1 and NP-2) have no signaling motifs in the intracellular domain and are thought of as passive co-receptors, enabling the interaction between semaphorins and plexins.

Some plexins form yet larger membrane complexes with and activate signaling receptors as Off Track (Otk) and the scatter factor receptors Met and Ron. A direct interaction between plexin A1 and the angiogenic Vascular Endothelial Growth Factor-receptor-2 (VEGFR2) has also been demonstrated (T. Toyofuku et al., E-publication in *Genes Dev.* 18:435-447 (2004)). Because NP-1 binds to plexin family members but also to VEGFR2, it is conceivable that multicomponent membrane protein complexes exist that encompass VEGFR2, NP-1 and plexins, establishing a link between plexins and angiogenesis (see also B. M. Weinstein, *Cell* 120:299-302 (2005)).

Neuropilins are also co-receptors for the potent angiogenic factor Vascular Endothelial Growth Factor-A (VEGF-$A_{165}$) and enhance its affinity for VEGFR2. Interestingly, the VEGF-$A_{165}$ binding site on NP-1 overlaps with that for semaphorin 3A (H. Q. Miao et al., *J. Cell. Biol.* 146:233-242 (1999)). It has been postulated that VEGF-A binding to NP-1 promotes migration of endothelial cells by competing for binding of class 3 semaphorins, which is generally followed by F-actin depolymerization and repulsion of cell extensions (R. E. Bachelder, *Cancer Res.* 63:5230-5233 (2003)). Similar antagonistic behavior of VEGF-A and class 3 semaphorins have been described in a neuronal progenitor cell line (D. Bagnard et al., *J. Neurosci.* 21:3332-3341 (2001)) and tumor cells (Bachelder (2003), supra). Since antagonistic effects were observed in tumor cells that are devoid of VEGF receptors, it is conceivable that the underlying mechanism involves members of the plexin family, establishing a further link between plexins and VEGF-A signaling.

The present inventors have previously found that the family member plexin D1 (plxnD1) is not only expressed in neuronal cells, but also in endothelial cells of the vasculature during early stages of development (B. van der Zwaag et al., *Dev. Dyn.* 225:336-343 (2002)), an observation that was confirmed by two other groups (A. D. Gitler et al., *Dev. Cell.* 7:107-116 (2004); J. Torres-Vazquez et al., *Dev. Cell.* 7:117-123 (2004)). In adult vasculature, plxnD1 is absent. Plxnd1-knockout mice and zebrafish carrying mutations in the plxnd1 gene are characterized by maldevelopment of the cardiovascular system (A. D. Gitler et al. (2004), supra; J. Torres-Vazquez et al., (2004), supra). Neuropilin-1 (NP-1) and NP-1Neuropilin-2 (NP-2) double knock-out mice also suffer from lethal defects in vascularization and aortic arch malformations during embryonic development (T. Kawasaki et al., *Development* 126:4895-4902 (1999); S. Takashima et al., *Proc. Natl. Acad. Sci. U.S.A.* 99:3657-3662 (2002); C. Gu et al., *Dev. Cell.* 5:45-57 (2003)).

Furthermore, morpholino-mediated knock-down of NP-1 in zebrafish leads to maldevelopment of intersegmental vessels and, in this model system, a clear link between NP-1 and VEGF-$A_{165}$ has been established (P. Lee et al., *Proc. Natl. Acad. Sci. U.S.A.* 99:10470-10475 (2002)). The resemblance of the phenotypes of plxnd1, neuropilin-1 and semaphorin 3C knock-out mice (L. Feiner et al., *Development* 128:3061-3070 (2001)) is consistent with the finding that Plexin D1 is a neuropilin-1-dependent receptor for semaphorin 3C (A. D. Gitler et al. (2004), supra). However, PlxnD1 is also a receptor for semaphorin 3E, and this interaction does not require neuropilins for Semaphorin 3E-mediated signaling (C. Gu et al., *Science* 307:265-268 (2005)).

According to the invention, it was now found that plexin D1 is also involved in angiogenesis during tumor growth and is expressed on the luminal side of endothelial cells in tumor blood vessels. Plexin D1 was furthermore found to be expressed by activated macrophages. Plexin D1 was also found to be expressed on tumor cells in a wide variety of tumor types.

The present invention thus relates to plexin D1 for use as a targetable protein in the treatment or diagnosis of disorders that involve expression of plexin D1.

Diagnosis is effected by detecting the presence of plexin D1 or a plexin D1-encoding nucleic acid in the body or a bodily tissue or fluid.

Treatment is effected by targeting plexin D1 for delivery of therapeutics to the site where treatment is needed, by interfering in the interaction between plexin D1 and its ligands, by interfering in the expression of the plexin D1 gene or by capturing plexin D1 ligands to inhibit interaction with plexin D1.

The invention thus furthermore relates to the use of molecules that bind plexin D1, a nucleic acid encoding plexin D1 or a ligand of plexin D1 for the preparation of a therapeutical composition for the treatment or diagnosis of disorders that involve expression of plexin D1. All these molecules will be identified herein as "binding molecules" or "binding entities."

The disorders comprise, in particular, disorders in which plexin D1 is expressed on tumor cells, tumor blood vessels or activated macrophages.

The tumor cells on which plexin D1 is expressed comprise brain tumors, in particular, astrocytomas, oligodendrogliomas and hemangioblastomas, colon carcinomas, in particular, ductal carcinomas of the colon, prostate carcinomas, renal cell carcinomas, in particular, renal clear cell carcinomas, mamma carcinomas, in particular, ductal carcinomas of the breast, ovary carcinomas, squamous cell carcinomas, melanomas, lung carcinomas, in particular, small-cell lung carcinomas and non-small-cell lung carcinomas, soft tissue sarcomas, etc.

When the disorders that are treated according to the invention are inflammatory diseases, they are, in particular, autoimmune disease, more in particular, rheumatoid arthritis, or they are atherosclerosis or multiple sclerosis.

Molecules that bind plexin D1 are, for example, selected from antibodies, antibody fragments, proteins, protein domains, peptides, and small molecules. These molecules can be used to target plexin.

Molecules that bind the nucleic acid encoding plexin D1 are, for example, oligonucleotides, such as RNA or DNA aptamers, for example, selected from siRNA, antisense RNA, and antisense phosphothio-oligonucleotides. These molecules can be used to interfere with the expression of plexin D1.

Molecules that bind a plexin D1 ligand are, for example, selected from antibodies against ligands, the soluble ectodomain of plexin D1 or small molecules, such as peptides, that bind plexin D1 ligands. These molecules can be used to capture circulating plexin D1 ligand, prevent binding of the ligand to plexin D1 on tumor vessel cells, tumor cells or activated macrophages and interfere with the function of plexin D1 on these cells.

For diagnosis, the binding molecule is suitably labeled with a detectable marker. Such a detectable marker is, for example, selected from a radioactive label, paramagnetic label, a fluorescent label, and a chemiluminescent label. Diagnosis can be performed in a sample of a bodily fluid or tissue in vivo, in situ or ex vivo. Examples of diagnostic techniques are in situ hybridization of, for example, plexin D1 mRNA or immunohistochemistry on biopsies or tumor cells.

For treatment, the binding molecule is, for example, provided with an entity that damages or kills the tumor cell and/or the tumor endothelial cell, in particular, a cytotoxic entity, such as a radionuclide, a toxin, boron for Boron Neutron Capture Therapy (BNCT), or a prodrug that is coupled to the binding entity via a cleavable linker, which is activated in response to cleavage of that linker, or apoptosis-inducing peptides, an example of which is the (KLAK-LAK)$_2$ (SEQ ID NO:7) sequence. Such peptides are added to the binding entity by molecular genetic engineering techniques.

The entities described above may be directly conjugated to the binding entity, or they may be present in nanodevices, such as liposomes or polymersomes, that are conjugated to the binding entity.

Boron Neutron Capture Therapy (BNCT) comprises irradiation of a diseased area, such as a tumor or an inflammation, in which boron has accumulated after intravenous injection of the liposomal conjugate, with neutrons, after which boron atoms will decay to lithium under emission of destructive alpha particles.

Alternatively, therapy may be effected by inducing local thrombosis in the tumor vessels to block the blood supply to the tumor and induce cell death. An example of such molecule is Tissue Factor (TF).

Advantageously, plexin D1 can be targeted with specific binding molecules upon intravenous administration since plexin D1 is expressed on the luminal side of endothelial cells in tumor blood vessels. Therapeutic compounds for damaging or killing tumor cells that are coupled to the binding molecule can reach the tumor from within and compounds that induce thrombosis are easily delivered to their site of action.

Interference with plexin D1 function represents a way to inhibit angiogenesis, to inhibit tumor cell migration, and to inhibit macrophage migration. Thus, the invention provides methods of treating or suppressing disorders in which plexin D1 is involved, by using the specific presence of plexin D1 to deliver therapeutics locally to diseased tissues, and/or by interference in the function of plexin D1 or in the interaction between plexin D1 and its ligands.

The invention is thus based on the fact that plexin D1 can be used as a targetable marker on tumor blood vessels, as a targetable protein involved in tumor angiogenesis, as a targetable marker on tumor cells, and as a targetable protein involved in cellular migration.

The invention thus also relates to the use of molecules that bind to plexin D1, its gene or mRNA or its ligands in diagnosis and therapy. All kinds of specific binding molecules, and derivatives thereof can be used in the invention, in particular, proteinaceous compounds, such as, but not limited to, antibodies, antibody fragments, single-domain antibody fragments, other proteinaceous binding domains, such as, but not limited to, lipocalins, and small molecules that specifically bind plexin D1 or its ligands. For binding to the plexin D1 gene or the mRNA transcribed from the plexin D1 gene, nucleic acid molecules, such as DNA or RNA, aptamers can be used.

In a first embodiment of the invention, plexin D1 or plexin D1 ligand binding molecules are antibodies, in particular, monoclonal antibodies, more in particular, human or humanized antibodies in which the constant regions of the original antibody are substituted with the constant regions of human antibodies, or fragments thereof, which still bind to plexin D1 or its ligand.

The antibody is preferably a human IgG1 antibody. However, other human antibody isotypes are also encompassed by the invention, including IgG2, IgG3, IgG4, IgM, IgA1, IgA2, IgAsec, IgD, and IgE. Also, all animal-derived antibodies of various isotypes can be used in the invention.

The antibodies can be full-size antibodies or antigen-binding fragments of antibodies, including Fab, F(ab')$_2$, single-chain Fv fragments, or single-domain VHH, VH or VL single domains.

Preferably, antibodies against plexin D1 are human monoclonal antibodies produced by a hybridoma cell, which includes a B cell obtained from an immunized transgenic animal having a genome comprising a human heavy chain transgene and a human light chain transgene, fused to an immortalized cell, or an animal-derived antibody or antibody fragment produced by a hybridoma cell, which includes a B cell obtained from an immunized animal, fused to an immortalized cell, or human and animal antibodies, produced by a eukaryotic cell transfected with the cDNA or genomic DNA encoding the antibody or antibody fragment.

In a preferred embodiment of the present invention, single-domain (VHH) Llama antibodies with affinity to plexin D1 are provided, more specifically, Llama single-domain antibodies A12 (SEQ ID NO:1) and F8 (SEQ ID NO:2), either or not displayed on M13 bacteriophages, also known to those with skill in the art as phage-display VHH antibodies.

A preferred single-chain antibody is derived from antibody 11F5H6 and 17E9C12. The sequence of the single-chain antibody is shown in SEQ ID NO:3 and SEQ ID NO:4.

The antibodies for use according to the invention may be high-affinity antibodies, which are evoked in non-transgenic laboratory animals, or in a transgenic animal in which the endogenous globulin locus has been substituted for the human globulin locus, thus allowing production of human antibodies in such animals (A. Jakobovits, *Curr. Opin. Biotechnol.* 6:561-566 (1995)).

The invention further relates to a method of producing the antibodies of the invention, comprising immunizing an animal with plexin DE or a cell expressing plexin DE or a nucleic acid encoding plexin DE or parts of the extracellular domain of plexin D1, such that antibodies against plexin D1 are produced by the B cells of the animal, isolating the B cells from the animal and fusing the B cells to a myeloma cell line to obtain immortalized cells that secrete the antibody. The animal is preferably a transgenic animal having a genome comprising a human heavy chain transgene and a human light chain transgene so that the resulting antibody is humanized.

In one embodiment, the method includes immunizing a laboratory animal with a synthetic peptide, chosen from the plexin D1 extracellular domain, for example, peptide 47-63 corresponding to the amino terminus of the mature plexin D1 amino acid sequence. Immunizations are, however, preferably done with recombinant extracellular domains, preferably a region with low similarity to other family members of the plexins, for example, a region comprising amino acids 47-546, lacking the Met-Related-Sequences. The recombinant plexin D1 extracellular domains can be produced in *E. coli* cells by inserting the coding nucleic acids in a suitable prokaryotic expression vector, for instance, under control of the β-galactosidase promoter, transformation of *E. coli* cells with the vector, and isolation of the recombinant proteins from purified inclusion bodies. It is preferred, however, that antibodies are evoked by immunization with the recombinant plexin D1 extracellular domain that is produced by eukaryotic cells, therefore, containing post-translational modifications that are most similar to those present in native plexin DE for example, by Chinese hamster ovary (CHO) cells after transfection with a vector, containing the coding nucleic acids for the extracellular domains under the control of a cytomegalovirus promoter. Recombinant extracellular plexin D1 fragments may or may not be fused to tags facilitating purification, e.g., a VSV tag or a constant region of a heavy chain of an immunoglobulin.

The method of producing the antibody may also comprise cloning the antibody coding regions from plexin D1-specific B-cells into an expression vector and expressing the coding sequence. In a preferred embodiment, the expression vector is pHENIXHISVSV, enabling expression by *E. coli* host cells of the antibody, flanked at the carboxyterminal end by a Vesicular Stomatis Virus (VSV-tag) and a His*8 tag. The VSV tag is meant to facilitate immunohistochemical detection, using specific antibodies. The His*8 tag is meant to facilitate purification based on Nickel affinity chromatography. Other expression vectors can likewise be used.

More specifically, the invention provides an isolated single-domain antibody A12, having a dissociation constant of less than $2\times10^{-8}$ M, which binds to the amino terminus of plexin D1 and which detects plexin D1 in immunohistochemical stainings and homes to plexin D1-expressing tumor blood vessels, and also to an isolated single-domain antibody F8, having a dissociation constant of less than $3\times10^{-8}$ M, which binds to the amino terminus of plexin D1 and which detects plexin D1 in immunohistochemical stainings and homes to plexin D1-expressing tumor blood vessels. Both isolated single-domain antibodies may be fused to the constant region of a human IgG1 heavy chain or the constant region of a mouse IgG1 heavy chain.

Preferably, fully human antibodies are used within the scope of the invention. In another embodiment, humanized or laboratory animal-derived antibodies may be used.

The invention further provides bispecific antibodies that have a binding specificity for plexin D1, and a binding specificity for a human antigen-presenting cell, or for an Fc receptor, wherein the Fc receptor is a Fc(gamma)R1 or a human Fc(alpha) receptor.

The invention also provides nucleic acid molecules encoding the preferred antibodies, or antigen-binding portions. Recombinant expression vectors that include nucleic acids that encode the antibodies of the invention, as well as host cells transfected with such vectors, are also encompassed in the invention.

Other binding molecules for use in the invention are small molecules that specifically bind to Plexin D1. The term "small molecule" refers often to molecules with molecular weights of 500 or below. The term is commonly used these days and thus clear to the skilled person. Moreover, small molecule libraries are already available or are being developed. An example of such library is the NIH Molecular Libraries Small Molecule Repository (MLSMR). Such libraries are subjected to High Throughput Screening (HTS) to identify molecules that bind to plexin D1. The invention also relates to the small molecules that result from a screen of such libraries.

Other compounds that can be used according to the invention comprise peptides or aptamers (Ulrich, *Med. Chem.* 1(2):199-208 (2005)) that bind to extracellular domains of plexin D1 and thereby interfere with binding of plexin D1 ligands to plexin D1. Conversely, such peptides or aptamers may also bind to the plexin D1 binding sites of the plexin D1 ligands and thereby interfere with ligand binding to plexin D1.

For interfering with the expression of the plexin D1 gene, another type of binding molecule is used, in particular siRNA, antisense RNA or antisense phosphothio-nucleotides. Small interfering RNA (siRNA) comprises small strands of RNA that interfere with the translation of messenger RNA. SiRNA binds to the complementary portion of the target messenger RNA and tag it for degradation, thus inhibiting gene expression. This is commonly known as gene "silencing." SiRNA is usually 21 to 23 nucleotides long. Antisense RNA is an RNA molecule transcribed from the coding, rather than the template, strand of DNA, so that it is complementary to the sense mRNA. Formation of a duplex between the sense and antisense RNA molecules blocks translation and may also subject both molecules to double-strand-specific nucleases, thus inhibiting expression of the gene. Inhibition of expression of the gene can be used to block angiogenesis and migration of tumor cells and macrophages.

Preferably, the above-described binding molecules bind to plexin DE its gene or its ligand in eukaryotic cells. The molecules specifically accumulate in tumors upon intravenous injection or specifically accumulate in tumor blood vessels upon intravenous injection.

The antibodies, fragments thereof, small molecules and other proteinaceous compounds that all bind plexin D1 can be used in various ways.

In one embodiment, the invention relates to compounds that bind to the extracellular part of plexin D1, which binding results in interference of plexin D1 function. Alternatively, the invention relates to compounds that bind to the intracellular domain of plexin D1 and that prevent signaling by plexin D1.

In a specific embodiment, such binding molecules bind to plexin D1 to interfere with the formation of multicomponent membrane complexes by inhibiting binding of plexin D1 ligands, in particular, neuropilin-1, neuropilin-2, semaphorin 3C, sempaphorin 3E, VEGF-receptor-1, VEGF-receptor-2 or VEGF-A, to plexin D1. Such binding molecules lead to inhibition of ligand-induced GTPase signaling by plexin D1 or to inhibition of migration of cells expressing plexin D1, in particular, tumor-associated endothelial cells, tumor cells or macrophages.

According to another aspect thereof, the invention relates to a method of inducing lysis of a cell expressing plexin D1, comprising contacting a cell expressing plexin D1 with the binding molecules, in particular, the antibodies, of the invention in the presence of human effector cells, such that lysis of the cell expressing plexin D1 occurs.

In a still further embodiment, the binding molecule is combined with or coupled to an effector compound that can detect the presence of plexin D1 for diagnostic purposes or that can perform an effect on the cell expressing plexin D1. The diagnostic or therapeutic effector compound can be directly coupled to the binding molecule or can be present in a transport vehicle, such as a nanodevice, in particular, a liposome or polymersome, that is coupled to the binding molecule. Alternatively, the binding molecule can be a bispecific antibody that binds both plexin D1 and the effector compound, thus targeting the effector compound to a site or cell where plexin D1 is expressed.

The invention thus provides in a particular embodiment thereof the use of such binding molecules in a method of diagnosing a disease mediated by expression of plexin D1, which method comprises intravenous delivery of the proteinaceous, aptameric or small molecule plexin D1 binding molecules, conjugated to an effector compound allowing in vivo detection of the binding molecules.

Diagnostic effector compounds are, for example, radioisotopes or contrast agents for Magnetic Resonance Imaging (MRI), such as gadolinium-DTPA, or fluorescent dyes.

Examples of radioactive substance comprise, but are not limited to, technetium$^{99m}$ ($^{99m}$Tc), iodine-123 ($^{123}$I), iodine-131 ($^{131}$I), rhenium-186 or -188 ($^{186/188}$Re), gallium-67 ($^{67}$Ga), the beta-radiation emitting substances yttrium-90 ($^{90}$Y) or lutetium-177 ($^{177}$Lu), and the positron emitting isotopes Fluorine-18 ($^{18}$F) and Carbon-11 ($^{11}$C). Such radioisotopes can be used to either detect or damage or kill cells expressing plexin D1. Usually, different isotopes are used for diagnosis and therapy. The skilled person is well aware of which isotope to use for which tissue and for which type of use.

In another embodiment, the proteinaceous, aptameric and small molecular binding molecules for use in the invention can be combined with or coupled to a toxic agent, such as chemotherapeutic agent either directly or in a transport vehicle, in particular, a nanodevice, such as a liposome or polymersome.

In another embodiment, a plexin D1 binding entity of the invention is coupled to one or more chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-[alpha]), monoclonal antibodies (e.g., trastuzumab and bevacizumab), recombinant toxins and immunotoxins (e.g., recombinant cholera toxin-B and TP-38), cancer gene therapies, and cancer vaccines (e.g., vaccine against telomerase).

Chemotherapeutic agents are preferably selected from the group consisting of doxorubicin, cisplatin, bleomycin sulfate, carmustine, chlorambucil and cyclophosphamide hydroxyurea. Other compounds are known to the person skilled in the art.

A tumor can also be treated by blocking its blood supply by inducing local thrombosis in the tumor vasculature. The binding molecules of the invention can, in this embodiment, be used to target thrombosis-inducing molecules, such as the blood coagulation co-factor TF (Tissue Factor), a radioactive entity or a toxin, such as ricin to the site of the tumor. Effector compounds can be coupled to the binding molecule, in particular, a plexin D1 binding molecule, or can be present in a nanodevice, such as a liposome or polymersome, that is coupled to the plexin D1 binding molecule.

An alternative method of treating cancer or an inflammatory disorder according to the invention is with boron. The binding molecules of the invention can be conjugated to transport vehicles, in particular, nanodevices, such as liposomes or polymersomes, that are filled with boron to obtain a therapeutic composition. After delivery and accumulation of this composition in the diseased area, this area is irradiated with neutrons, resulting in emission of radioactive and cytotoxic alpha-particles that damage or kill the tumor endothelial cells, tumor cells and/or activated macrophages.

It is desirable for tumor blood vessel targeting antibodies to have high affinities toward plexin D1, for example, higher than $10^{-8}$, preferably higher than $10^{-9}$, more preferably higher than $10^{-19}$ M. High affinity and the high molecular weight of antibodies will, however, restrict penetration into tumor tissue. Therefore, the nucleic acids that encode the monoclonal antibodies obtained via RT-PCR cloning, can be used to generate antibody derivatives, for example, antibodies that lack the constant region and are monovalent, or antibody fragments that are adapted to optimal affinities for blood vessel targeting or tumor penetration by mutagenic procedures. These antibody derivatives will have lower affinities and lower molecular weight and will have improved tumor cell targeting properties.

Different binding molecules of the invention can be combined in a mixture. In a specific embodiment, the members of the mixture have a varying affinity. An example of such a combination is a mixture of monoclonal antibodies and/or antibody fragments or a mixture of antibodies with small molecules. The monoclonal antibodies having high affinity can be used for targeting vessels, whereas the smaller fragments having a lower affinity are better able to penetrate and reach the tumor cells. Alternatively, a mixture of plexin D1 binding molecules can be used together with plexin D1 ligand binding molecules and/or with molecules that bind nucleic acids encoding plexin D1, or plexin D1 ligand binding molecules can be combined with molecules that bind nucleic acids encoding plexin D1.

The plexin D1 binding molecules of the invention can be used in a method of treating a disease mediated by expression of plexin D1, comprising intravenous delivery of the binding molecules of the invention at a dose effective in treating that disease.

The binding molecules can also be used in a method of diagnosing a disease mediated by expression of plexin D1, comprising intravenous delivery of conjugates of plexin D1 binding molecules with a paramagnetic, fluorescent or radioactive tracer followed by magnetic resonance imaging, optical imaging, SPECT or PET.

The binding molecules can further be used in a method of treating or suppressing a disease mediated by expression of plexin D1, comprising intravenous delivery of the proteinaceous and small molecular binding molecules of the invention or a composition of proteinacous and small molecular binding molecules.

The disease to be treated or diagnosed can be cancer, an inflammatory disease, in particular, an autoimmune disease, such as rheumatoid arthritis, or atherosclerosis, or multiple sclerosis.

Diagnosis can be performed in vivo and in vitro. An in vivo method is described above and can be performed with magnetic resonance imaging (MRI) or with SPECT or PET cameras after accumulation of the radioactively labeled binding molecule in the diseased tissue.

Another diagnostic method comprises detecting the presence of plexin D1 in a sample in vitro or ex vivo. Such method comprises contacting the sample with binding molecules of plexin D1, or nucleic acids that bind the plexin D1 gene or its mRNA or a copy DNA derived from this mRNA, all bound to a detectable marker, under conditions that a complex between the antibody and plexin D1 forms, and detecting the formation of the complex. The complex can be detected by visualizing the detectable marker. Samples can be bodily fluids, such as blood, serum, plasma, saliva, urine, semen, feces, or tissues, such as biopsies of tumor cells.

The invention further relates to an expression vector, comprising the coding sequence for Llama antibody F8 or A12, or for the single-chain antibody derived from antibody 11F5H6 and suitable regulatory sequences. The invention also relates to a cell transfected with the expression vector. The invention further relates to the recombinant protein obtainable by expressing the expression vector.

Another aspect of the invention relates to an expression vector, comprising the coding sequence for the extracellular domain of plexin D1, optionally fused to a constant region of a human heavy chain and suitable regulatory sequences. The invention also relates to a cell transfected with the expression vector. The invention further relates to the recombinant protein obtainable by expressing the expression vector.

The recombinant protein comprises the extracellular domain of plexin D1, which binds to plexin D1 ligands and thus prevents binding of the ligands to cell-associated plexin D1. Preferably, the coding sequence codes for a recombinant protein comprising amino acids 47-506 of the extracellular domain of plexin D1, which binds to plexin D1 ligands and thus prevents binding of the ligands to cell-associated plexin D1, or amino acids 507-1274 of the extracellular domain of plexin D1, which binds to plexin D1 ligands and thus prevents binding of the ligands to cell-associated plexin D1. Such recombinant protein may carry mutations that increase the affinity for plexin D1 ligands and thereby having increased potency as decoy receptor. Such mutations are usually induced by making changes in the coding sequence used for producing the recombinant protein.

The invention further relates to the use of the binding molecules of the invention in a method of treating or suppressing a disease mediated by plexin D1, comprising intravenous or intratumoral delivery of decoy plexin D1 extracellular domains as described above, or in a method of treating or suppressing a disease mediated by plexin D1, comprising intravenous delivery of adenoviruses or lentiviruses, containing the coding nucleotides for the recombinant extracellular domains of plexin D1 or parts thereof as described above.

These antagonistic decoy plexin D1 receptors interfere with the interaction between plexin D1 and its ligands, in particular, neuropilin-1, semaphorin 3C and sempahorin 3E, and thereby interfere with plexin D1 function.

Preferably, the decoy plexin D1 receptors have increased affinity toward plexin D1 ligands, as compared to plexin D1. Such increased affinity may be obtained by creating a library of plexin D1 extracellular domains, carrying at random introduced mutations, and selecting decoy receptors with most potent antagonistic behavior in cell migration assays.

In order to produce the proteinaceous molecules (including peptides, polypeptides and glycosylated polypeptides or polypeptides having other post- or peritranslational modifications), it is desirable to insert the recombinant nucleic acid that encodes fragments of the extracellular domain of plexin D1 that comprise the binding sites for semaphorin 3C, semaphorin 3E and NP-1 into expression vectors. The antagonists according to the invention are preferably produced from a nucleic acid or an expression vector according to the invention, preferably in a host cell.

The molecules of the invention may also be used in a combination of treatment methods as described above and/or with conventional therapies or anti-angiogenic therapy for further preventing the formation of a tumor neovasculature, or radiotherapy and/or adjuvant chemotherapy.

The invention further relates to a method of identifying molecules that are capable of binding to plexin D1, which method comprises contacting a collection of molecules with plexin D1 and selecting the molecules from the collection that show binding to plexin D1 as plexin D1 binding molecules. The collection of molecules can, for example, be present in small molecule libraries, on a protein array, etc. The techniques for screening collections of molecules are in itself known. The invention resides in the identification of the target that is to be bound, which is plexin D1.

In this disclosure, the term "binding molecule" is used for all types of binding molecules, i.e., the ones that bind plexin D1, the ones that bind a nucleic acid encoding the plexin D1 gene, and the ones that bind plexin D1 ligands. All these types of molecules can be coupled to effector compounds as described above.

BRIEF DESCRIPTION OF THE FIGURES

The present invention will be further illustrated in the Examples that follow and that are in no way intended to limit the invention. In the Examples, reference is made to the following figures:

FIG. 2: Panel A) In situ hybridization analysis of cerebral Me157-VEGF-$A_{165}$ lesions using a digoxigenin-labeled mouse-specific plxnd1 RNA probe. Tumor vessels are strongly positive (arrows) whereas brain capillaries, distant from the lesions, are negative (compare the ISH profile with the CD34 staining in FIG. 2, Panel B).

Kinetic measurements were performed at 25° C. with a flow rate of 10 ml/minute in HBS-EP buffer (10 mM Hepes, pH 7.4, 150 mM NaCl, 3 mM EDTA, 0.005% surfactant P20). Six concentrations of Ni-affinity-purified sdabs (in the range of 1 mM to 50 µM) were used to determine the dissociation constants (Kds) of the interaction with the PLXND1-peptide. After each experiment, regeneration of the sensor surface was performed with 10 mM NaOH.

Specific binding, defined by binding to a PLXND1-surface minus binding to a control BSA-surface, was analyzed using the BIAevaluation 4.1 software and a 1:1 Langmuir binding model. Affinities of single-domain antibodies A12 and F8 were $2.1 \times 10^{-8}$ M and $3.5 \times 10^{-8}$ M.

Figure 7:
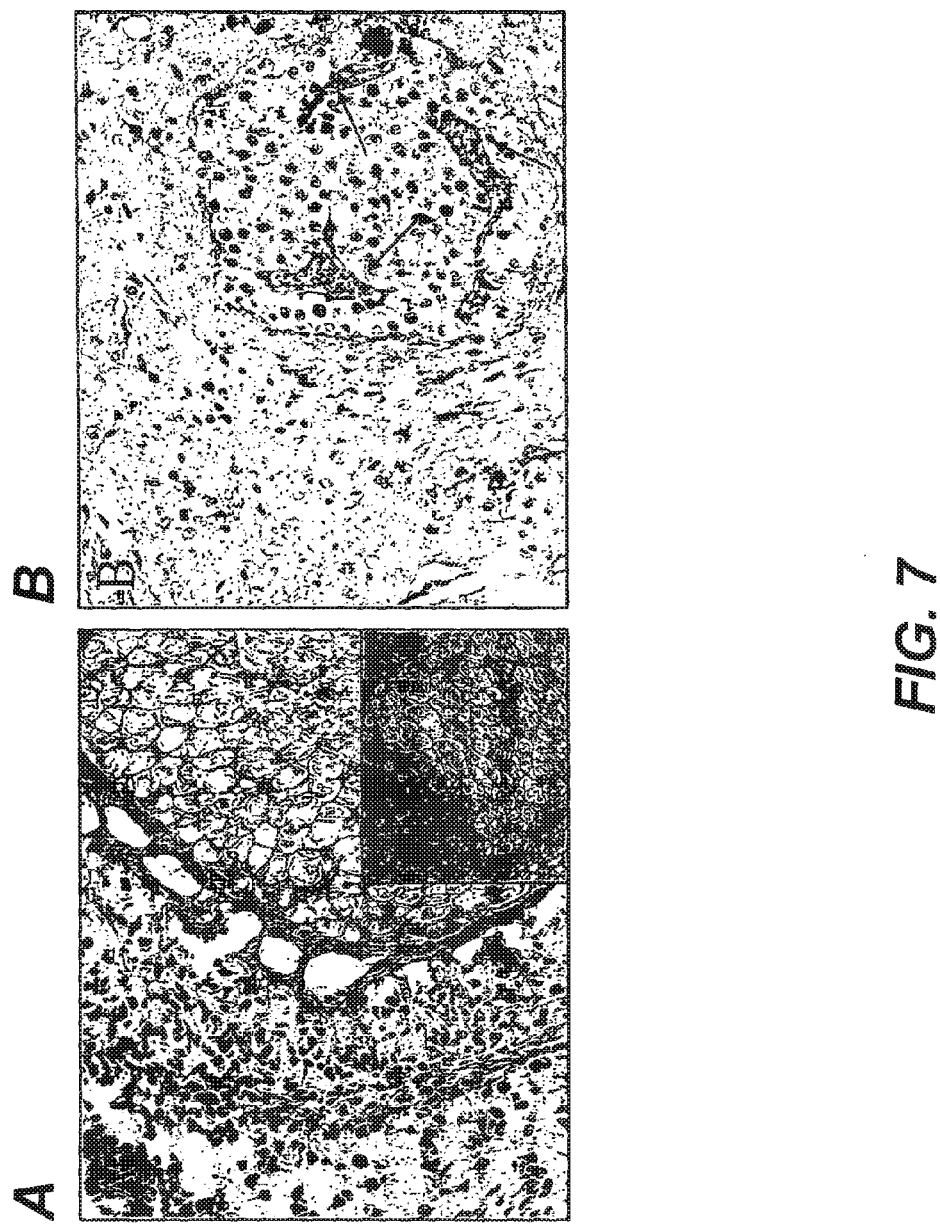

FIG. 7: Evaluation of plexin D1 specificity of single-domain antibodies. Panel A shows immunohistochemical staining of the growth plate of trabecular bone of a mouse embryo (E16.5) with single-domain antibody A12, utilizing the VSV-G tag for detection of the antibody. The inset shows an in situ hybridization of a similar embryonic structure using a mouse-specific digoxigenin-labeled plexin D1 probe. Note the overlap of plexin D1 in situ hybridization and immunostaining. Panel B is a representative example of a Me157-VEGF-$A_{165}$ lesion in brain of a nude mouse. The vasculature, which is also positive in plexin D1 ISH (see also FIG. 2), is immunopositive with single-domain antibody F8.

Figure 8:
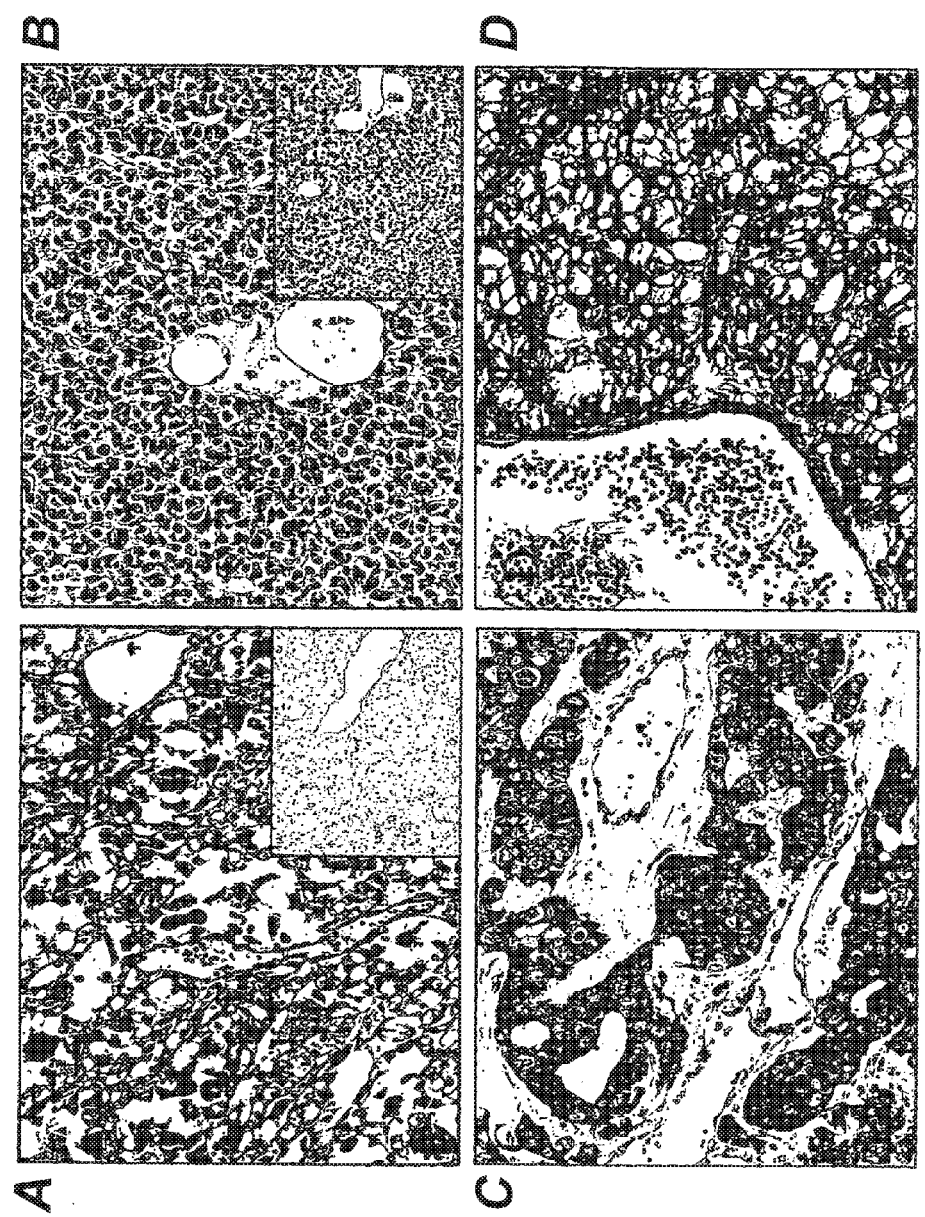

FIG. 8: Immunostainings with single-domain antibody A12 on a selection of human brain tumors. Tumors shown are (Panel A) glioblastoma multiforme, metastases of (Panel B) melanoma (Panel C) mammacarcinoma and Panel D) renal cell carcinoma. The insets in Panels A and B consist of control stainings with anti-VSV antibody only, and show that the tumor staining is specific. Note that vessels and tumor cells are highly reactive with the antibody.

Figure 9:
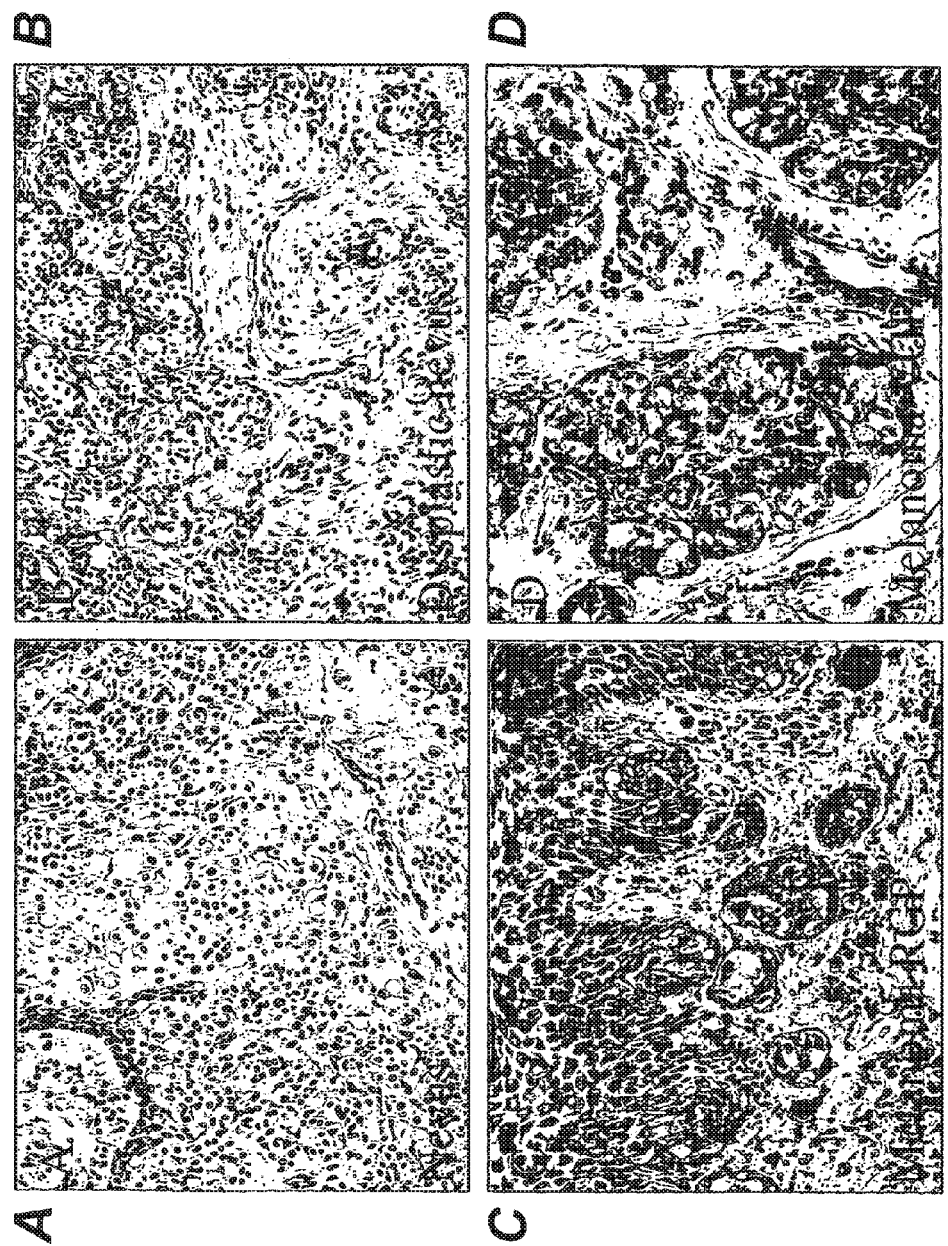

FIG. 9: Immunostainings with single-domain antibody A12 on a progression series of melanoma. Immunostainings were performed on a nevus, a dysplastic nevus and horizontal and vertical growth phases of melanoma. Note that only the neoplastic cells express plexin D1.

Figure 10:
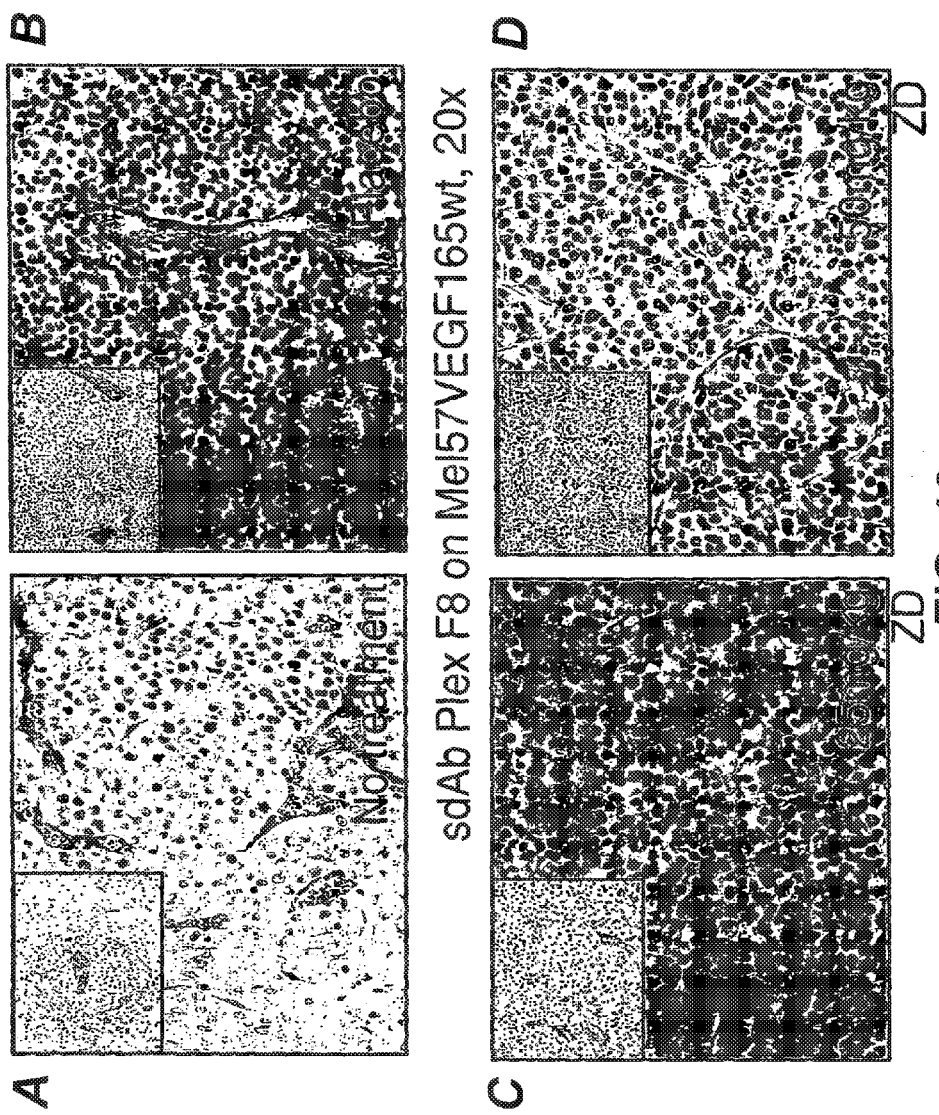

FIG. 10: Immunostainings with single-domain antibody A12 on sections of Me157-VEGF-A brain tumors in mice, treated with ZD6474. In untreated or placebo-treated mice, tumor vessels stain positive with this antibody. However, in ZD6474-treated mice, there is a dose-dependent decrease of plexin D1 expression. ZD6474 was given orally, once daily, in the dosage as indicated.

Figure 11:
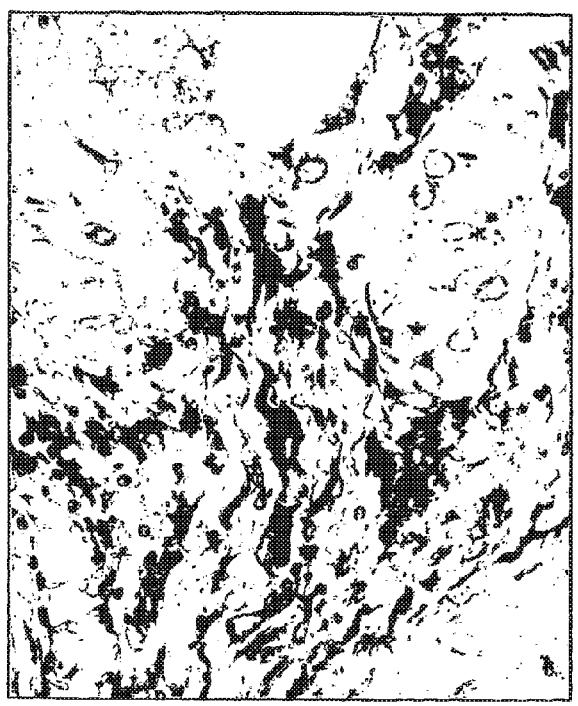

FIG. 11: Double immunostainings with the macrophage marker CD68 and single-domain antibody A12 on mammacarcinoma. A subpopulation of macrophages express plexin D1 as revealed by a staining protein.

Figure 12:
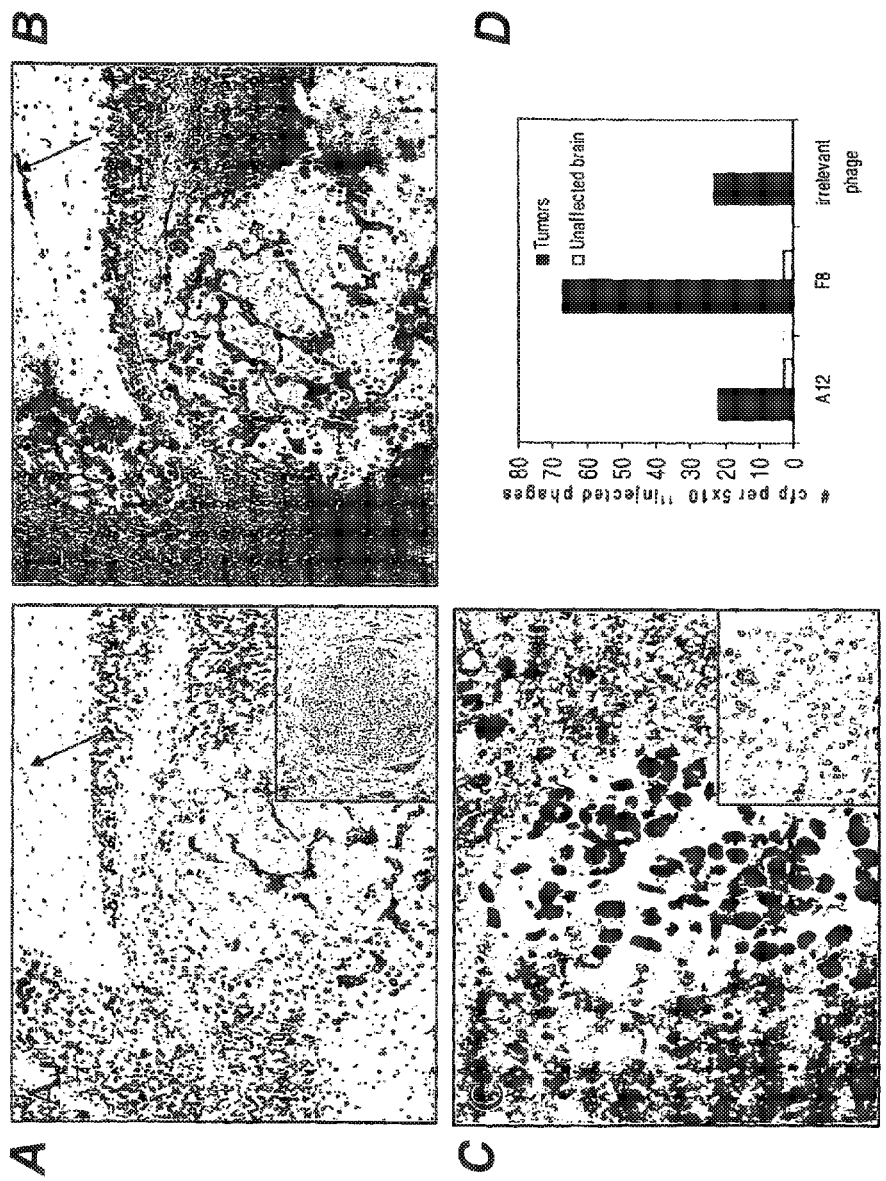

FIG. 12: In vivo homing of phage A12, F8 or an irrelevant phage to Me157-VEGF$_{165}$ brain lesions. Tumor-bearing mice were injected with $10^{12}$ phages in the tail vein and, after 5 minutes, mice were anesthetized and subjected to cardiac perfusion with 15 ml of phosphate-buffered saline. Mice were sacrificed, brains removed and frozen sections were analyzed for phage content and distribution. Panel A) M13 staining of a frozen section of brain Me157-VEGF$_{165}$ lesions. Phages are clearly vessel-associated, as evidenced by the anti-CD34 immunostaining on a serial section, shown in Panel B). The arrows point at a CD34-positive vessel, distant from the lesion, which is not highlighted by anti-M13 staining. The inset in Panel A shows a control experiment where an irrelevant phage was injected. Panel C) Distribution of sdab F8 after intravenous injection in tumor-bearing mice. Sdabs are visualized by immunohistochemistry using an anti-VSV antibody. Note that the sdab is detected in tumor vessels but not in normal brain capillaries. The inset shows the control experiment where an irrelevant sdab was injected. An interstitial localization was observed, consistent with the leaky nature of the vessels in these tumors. Panel D) Quantification of phage homing. Tumor tissue was dissected from 10 µm frozen sections using laser capture dissection microscopy. Number of colony-forming phages (cfp) were counted after infection of TG1 cells. Twenty-fold more F8 phages were eluted from tumors than from comparable areas of unaffected brain tissue.

Figure 13:
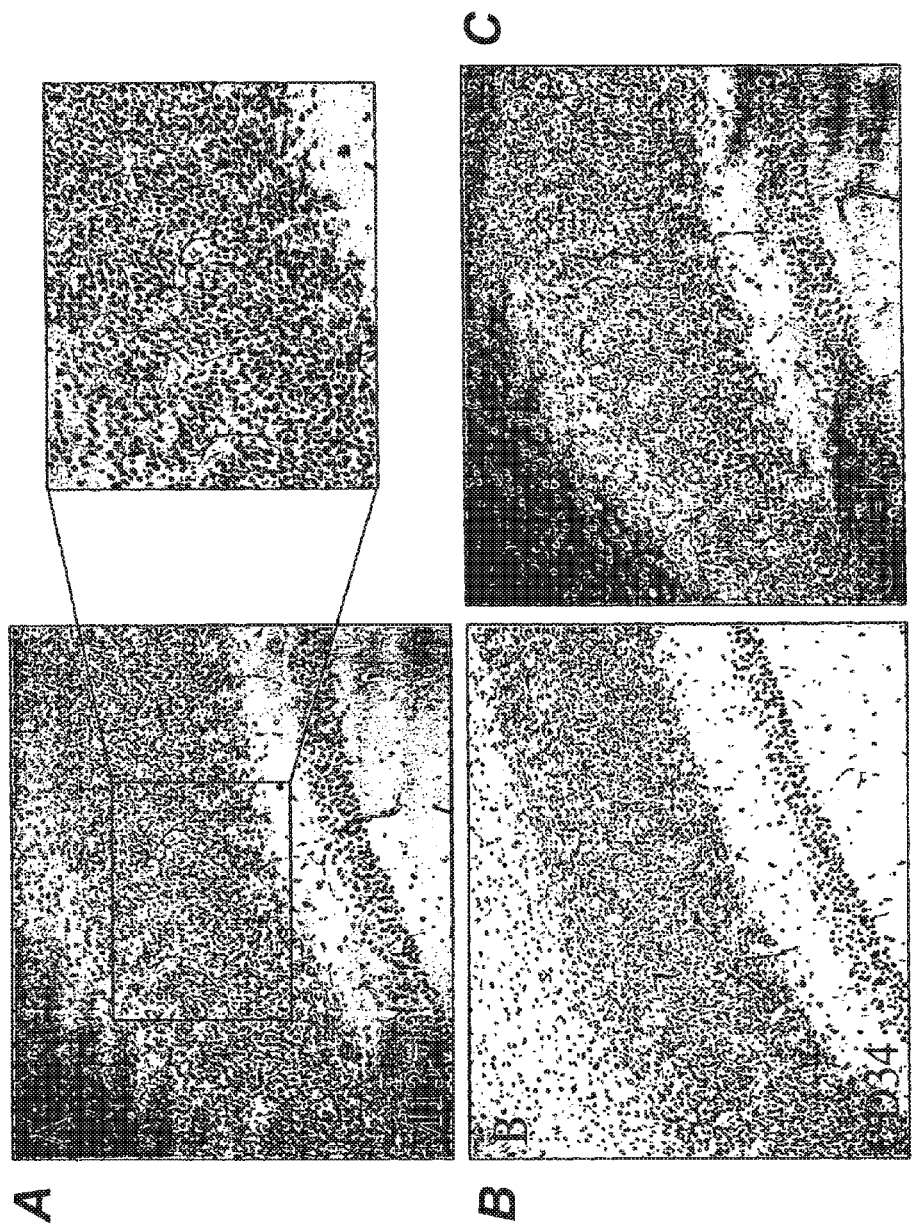

FIG. 13: Single-domain antibody homes to tumor vessels that are not per se newly formed. Nude mice were inoculated with a cell suspension of $1.5 \times 10^5$ cells of the human glioma xenograft E98, which was obtained from a subcutaneous E98 tumor. After 3 weeks, phages carrying single-domain antibody F8 were injected in the tail vein, and after 5 minutes, mice were anesthetized and subjected to cardiac perfusion using 15 ml of phosphate-buffered saline. Mice were then sacrificed, brains removed and fixed in formalin. Serial sections were stained with antibodies against M13 p8 protein (Panel A), the endothelial marker CD34 (Panel B) and glut-1 (Panel C, a marker for pre-existent brain capillaries). Comparison of Panels A, B and C reveals that not only newly formed tumor vessels accumulate phage F8, but also non-dilated brain vessels that express glut-1, and that, therefore, are considered pre-existent brain vessels that had been incorporated in the tumor.

Figure 14:
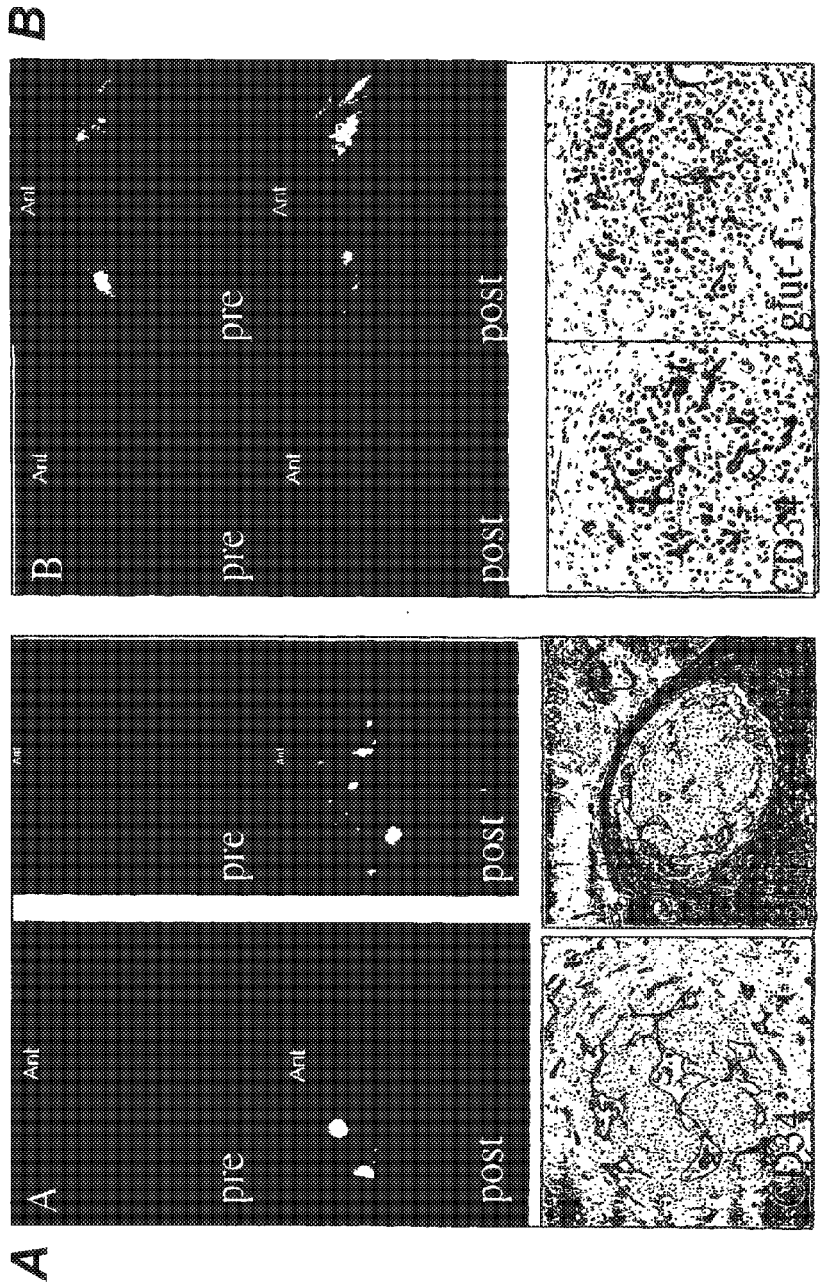

FIG. 14: Effects of extracellular domains of plexin D1 on the development of tumor vasculature. Double transfectants of the human melanoma cell line Me157, expressing VEGF-$A_{165}$ and the extracellular domain of plexin D1 comprising amino acids 1-850, were injected in the right internal carotid artery of nude mice. After three weeks, the mice were subjected to Gadolinium-DTPA-enhanced magnetic resonance imaging. Panel A shows MR images of two control mice carrying Me157 brain tumors that express VEGF-$A_{165}$ only. Panel B shows MR images of brains of two mice carrying the double transfectant. Vascular leakage, as assayed by Gd-DTPA extravasation, tends to be less in the double transfectants, suggesting that VEGF-A-induced vascular leakage is counteracted by the plexin D1 ectodomain. More importantly, blood vessels in the double-transfected tumors are activated, as indicated by upregulation of CD34, yet they express glut-1, strongly suggesting that these vessels are pre-existent vessels that are incorporated in the tumor by the phenomenon of co-option. Note that the blood vessels in the tumors expressing VEGF-$A_{165}$ only, are negative for glut-1 and, therefore, can be considered to be newly formed.

Figure 15:
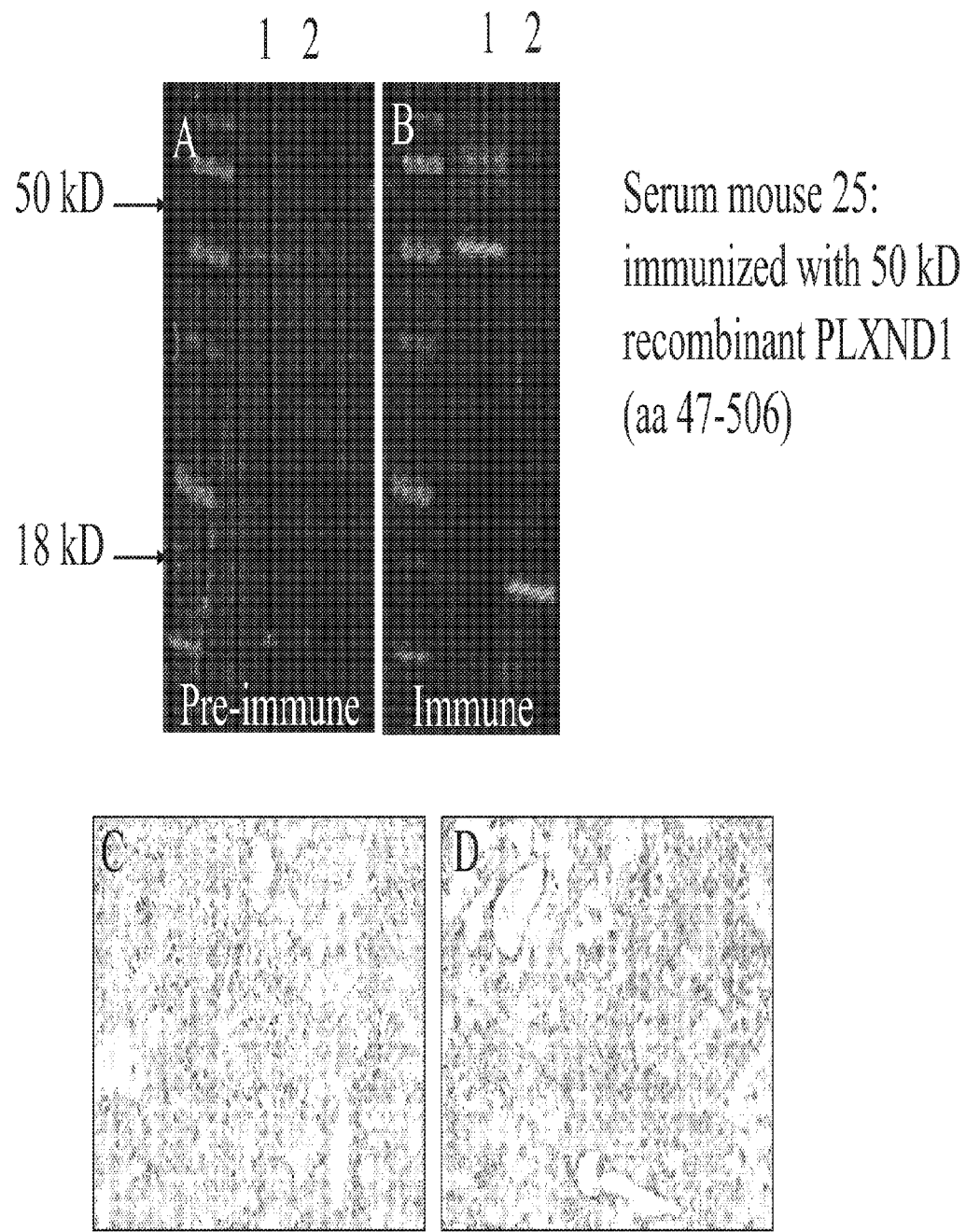

FIG. 15: Western blots were generated with recombinant plexin D1 ectodomains, expressed in *E. coli* and encompassing amino acids 47-506 (lanes 1) or 225-388 (lanes 2). Serum of mouse 25 was tested before (Panel A) and after (Panel B) immunization with plexin D1 region 47-506. As shown in Panel B, the mouse immune serum specifically recognized *E. coli* recombinant protein 47-506 (52 kDa, lane 1) and the protein encompassing plexin D1 residues 225-388 (a 18 kDa protein that lies completely within the sequence that was used for immunization, lane 2). The pre-immune serum did not show such a reactivity (Panel A). When tested in immunohistochemical stainings on a brain metastasis of an alveolar soft tissue sarcoma, the mouse immune serum (Panel D), but not the pre-immune serum (Panel C), showed positivity toward blood vessels and tumor cells, a staining pattern that was similar to that of single-domain antibody A12.

Figure 16:
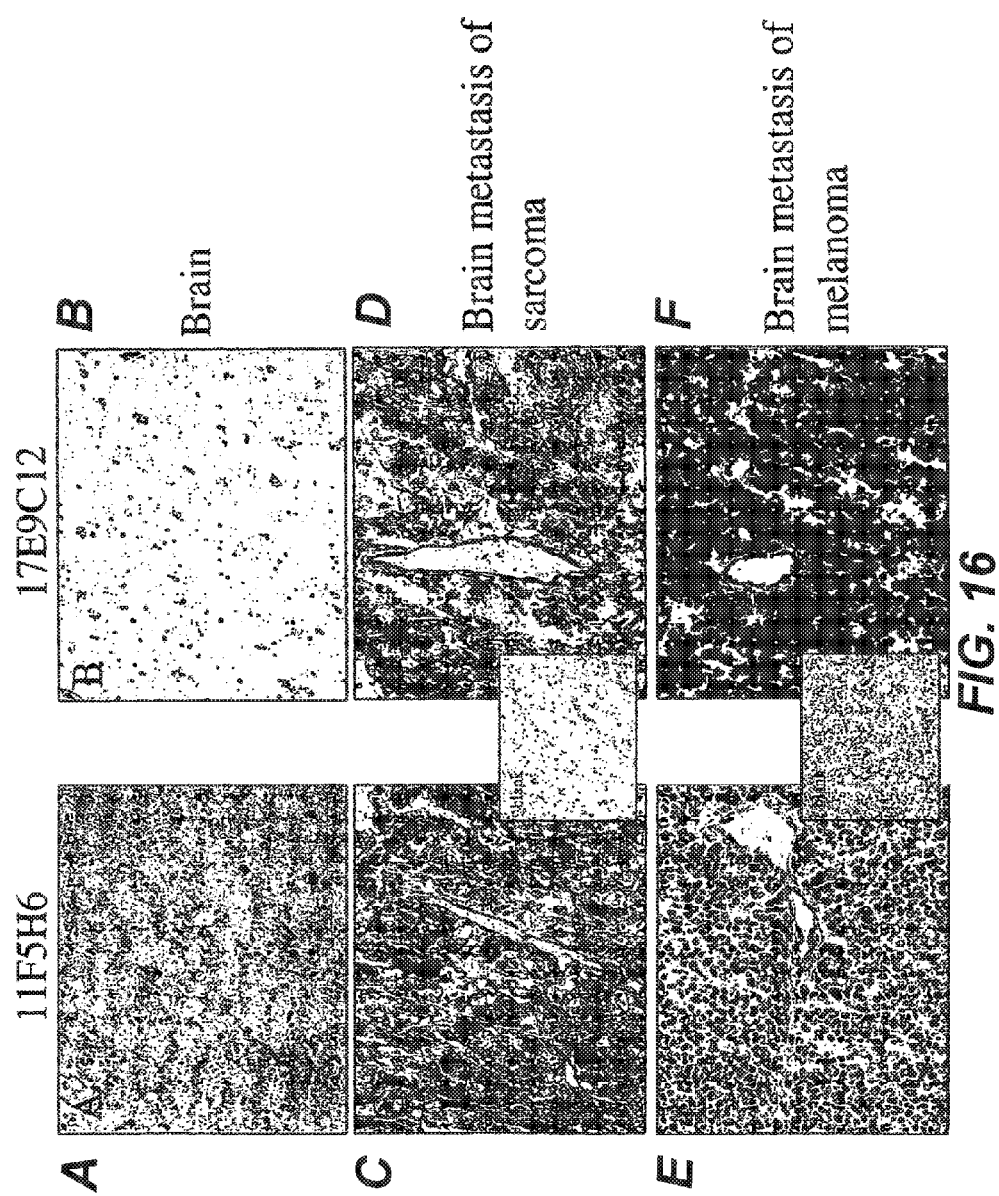

FIG. 16: Immunohistochemistry with monoclonal 1 μM antibodies, obtained from B-lymphocytes from mouse 25. Antibodies 11F5H6 and 17E9C12 were selected based on reactivity against protein 47-506 in ELISA, and were analyzed for their potential to detect plexin D1 in frozen sections of human tumors. These antibodies showed strong positivity in brain metastases of sarcoma and melanoma, as illustrated in the figure. Of note, the insets in Panels C-F represent control stainings in which the primary antibody was omitted. Panels A and B show that these antibodies do not notably recognize vessel structures in normal brain tissue.

Figure 17:
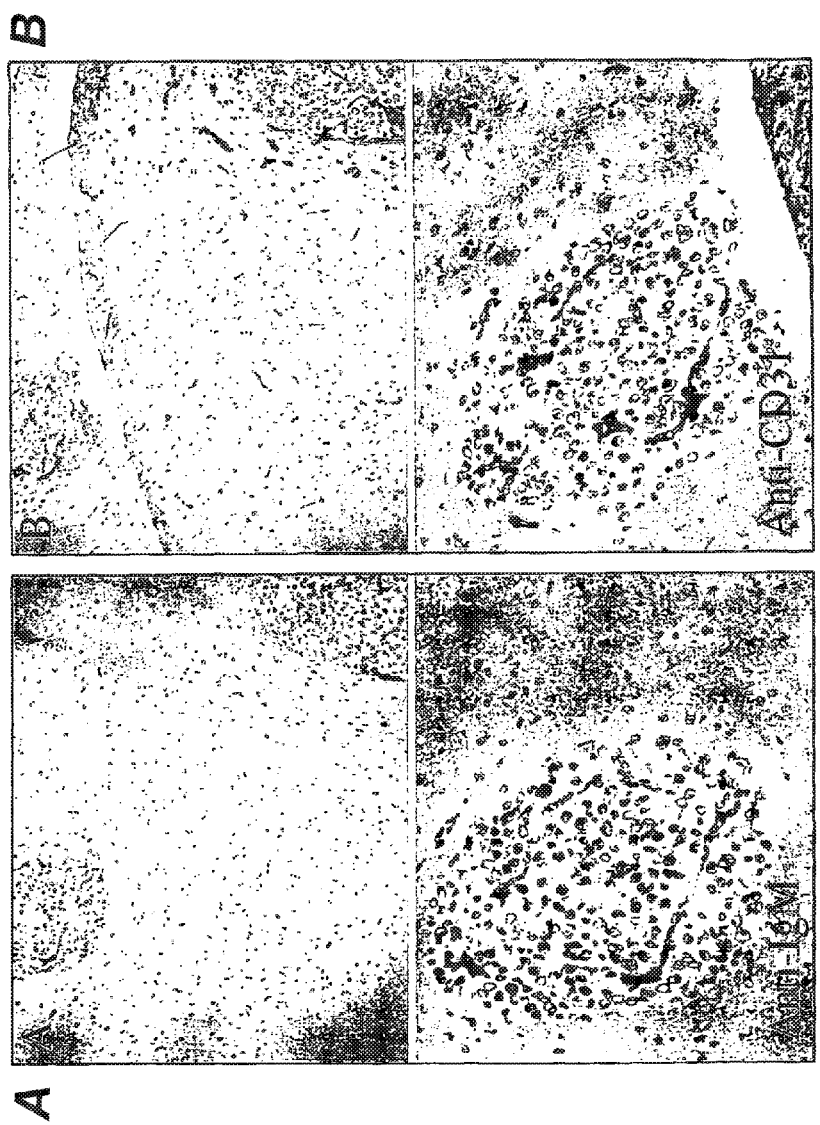

FIG. 17: Tumor homing of antibody 11F5H6. To further evaluate whether monoclonal antibody 11F5H6 is able to recognize tumor blood vessels, angiogenic Me157-VEGF-A tumors were grown in brains of nude mice, essentially as described in Example 10. Antibody 11F5H6 (1 mg) was injected in a lateral tail vein and allowed to circulate for 15 minutes. After this period, the mice were anesthetized with 1.3% isoflurane and the chest was opened, upon which a cardiac perfusion was performed with 20 ml phosphate-buffered saline. After this procedure, mice were decapitated, and brains removed and snap-frozen or fixed in formalin. Frozen sections of 4 μm were stained with anti-IgM antibody. In FIG. 17, Panel A, it is shown that antibody 11F5H6 homes to and accumulates in tumor vessels but not in normal vessels (compare anti-IgM staining in Panel A with the anti-endothelial CD31 staining in Panel B). Such staining is not seen when performing anti-IgM staining on non-injected mice. Thus, 11F5H6 is a promising antibody that allows tumor targeting.

Figure 18:
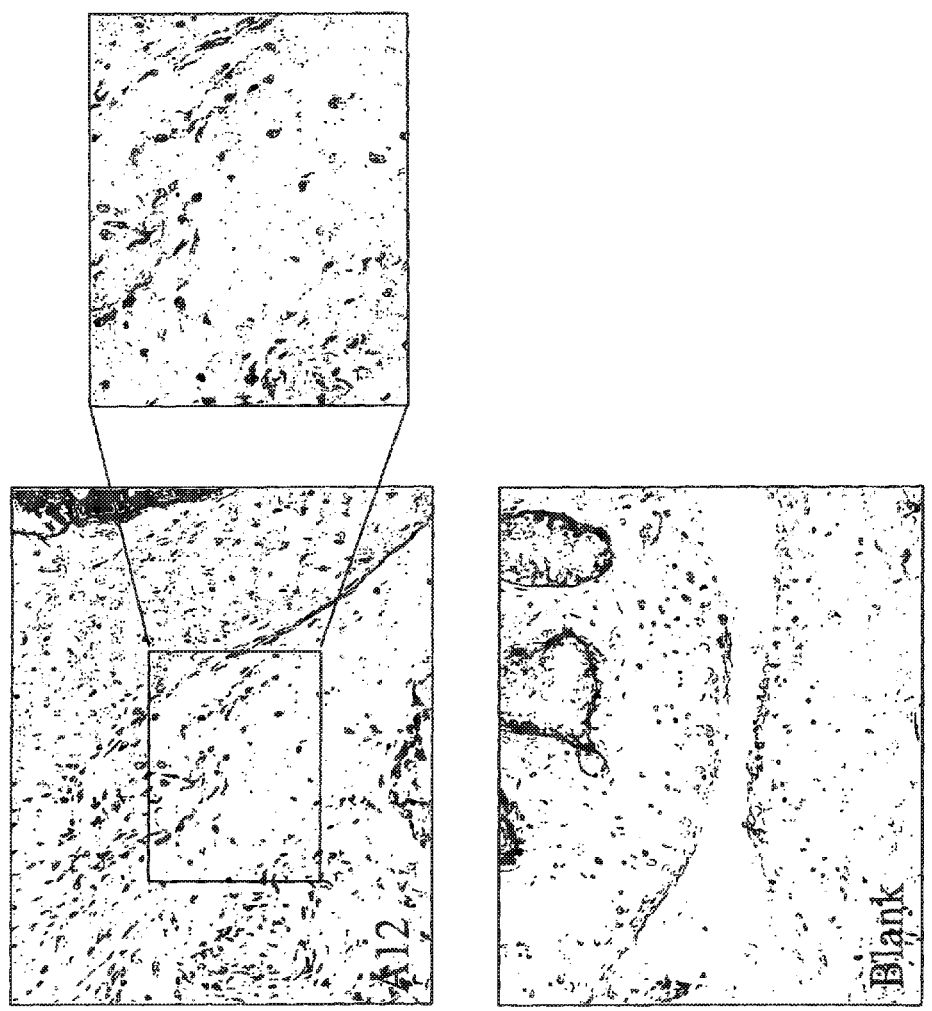

FIG. 18: Expression of Plexin D1 in macrophages in a mouse model of rheumatoid arthritis. Stainings were performed with single-domain antibody A12.

Figure 19:
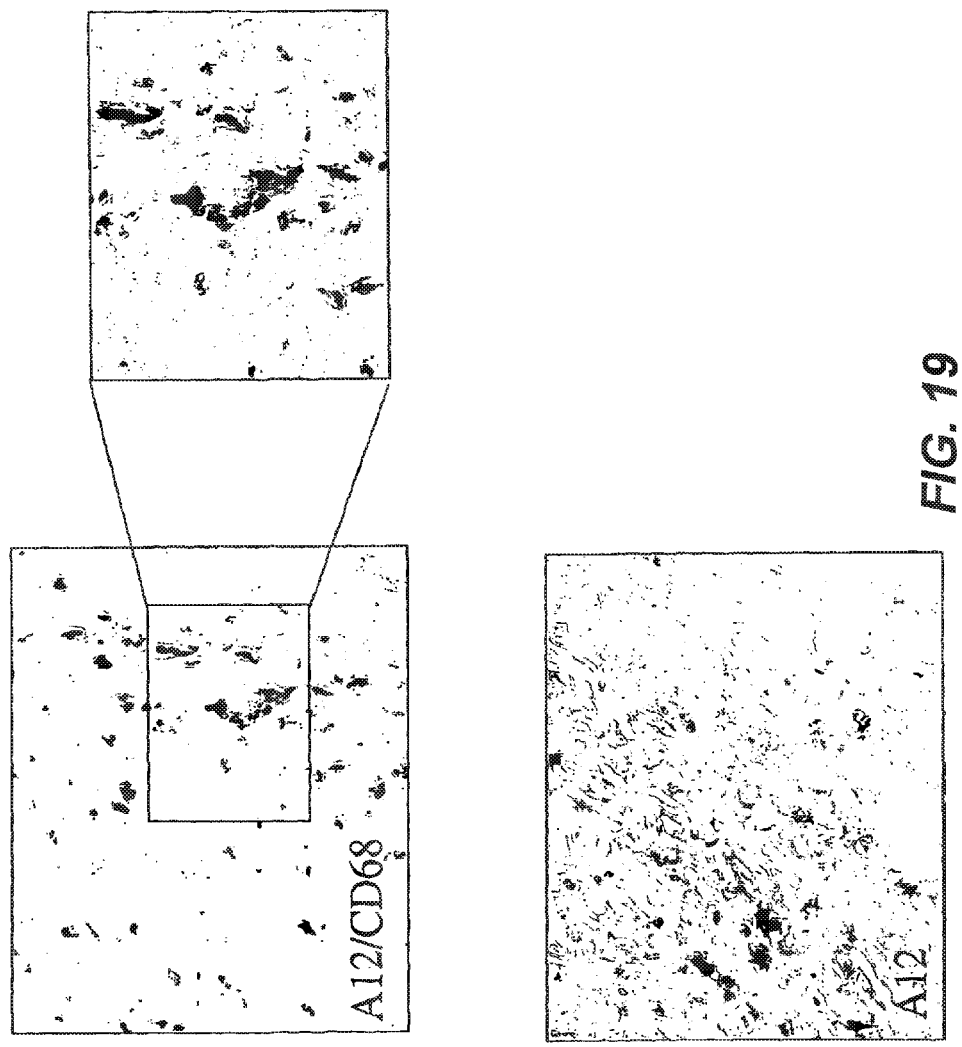

FIG. 19: expression of Plexin D1 in atherosclerosis. A subset of macrophages in human atherosclerotic plaques expresses plexin D1. Stainings were performed with single-domain antibody A12. A double staining was performed, displaying plexin D1 in red and the macrophage marker CD68 in blue. A purple color indicates co-expression.

The tables show the following:

Table 1: Analysis of different pathologies for plexin D1 expression.

Table 2: Plexin D1 expression in melanocytic lesions increases from benign to malignant lesions.

DETAILED DESCRIPTION

EXAMPLES

Example 1

Specific Expression of Plexin D1 on Tumor-Associated Blood Vessels

Plexin D1 is expressed on neurons but also endothelial cells in angiogenic vessels during embryogenesis.

The present invention demonstrates that plexin D1 is expressed on tumor-associated blood vessels but not on normal blood vessels. This has been shown by in situ hybridization of mouse brains, containing angiogenic human melanoma lesions (FIG. 2). The animal tumor model is described in (B. Kusters et al., *Cancer Res.* 63:5408-5413 (2003)). In short, tumor cells are injected via a microsurgical procedure in the right carotid artery, resulting in tumor growth in the parenchyma of the right brain hemisphere. After three weeks, at the onset of neurological symptoms, mice are sacrificed and brains removed and fixed in formalin.

Sections of 4 μm were subjected to in situ hybridization with digoxigenin-labeled sense and antisense RNA fragments. RNA probes were generated by transcription using T3 and T7 RNA polymerase, respectively, from a PCR product, encompassing 600 bases in the 3'-untranslated region, and which was flanked by T7 and T3 promoters (Van der Zwaag et al. (2002), supra).

In situ hybridizations using antisense RNA probes and sense RNA probes as negative controls, were performed using standard protocols. Sections were deparaffinated by melting paraffin at 60° C. and subsequent treatments with xylene and ethanol. After rehydration in phosphate-buffered saline (PBS), a proteinase K digestion was performed (10 μg/ml PBS in 20 mM Tris-HCl pH7.4/5 mM EDTA) for 15 minutes at 37° C. Sections were post-fixed in 4% buffered formaldehyde for 10 minutes, and acetylated in 0.1 M acetic acid anhydrid. Slides were washed subsequently in 2×SSC (sodium Citrate/sodium chloride) and MILLIQ®. After drying, slides were hybridized with digoxigenin-labeled RNA probes overnight at 65° C. in 50% formamide/2×SSC.

High levels of plexin D1 RNA were observed in vessels of angiogenic Me157 tumors (FIG. 2) using a mouse-specific plexin D1 RNA probe. Tumor cells were also positive for the transcript. The non-perfect homology between mouse and human plexin D1 results in a weaker signal in the human tumor cells using the mouse probe.

Example 2

Expression of Plexin D1 in Tumors

Figure 1:
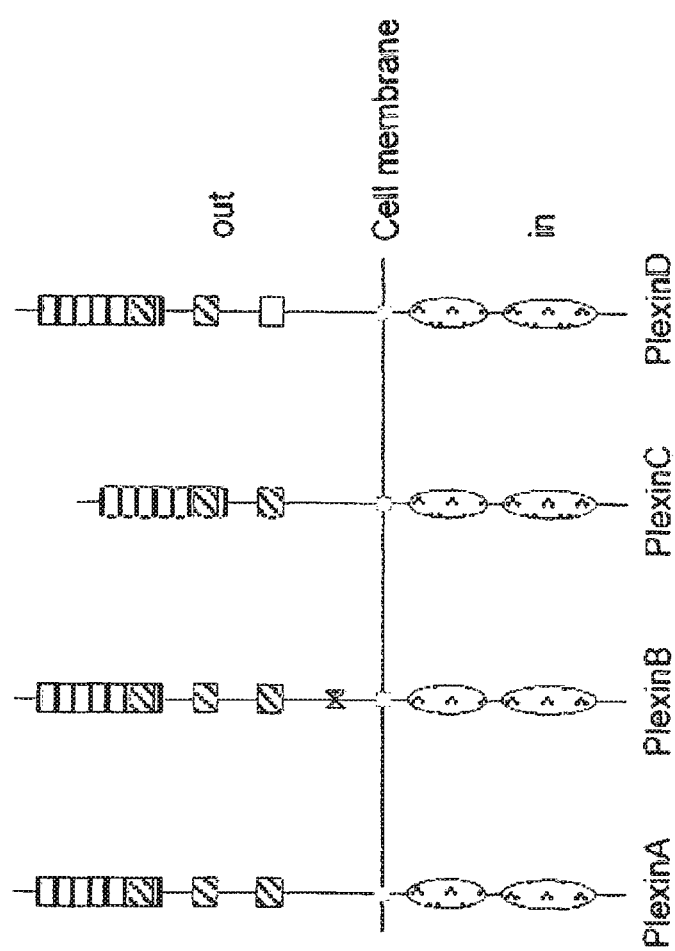
FIG. 1: Structural domains of plexin family members: four subfamilies have been identified, named PlexinA-PlexinD. Horizontally hatched boxes indicate Sema domains, diagonally hatched boxes indicate Met-related sequences (MRS) motifs, and the clear box indicates the atypical MRS motif of PLXND1. PlexinB subfamily members have a potential furin-like proteolytic site, marked by a grey ribbon. The transmembrane region is marked by a shaded box and is followed by two conserved intracellular domains, together comprising the SP-domain, marked by two ovals.
Figure 3:
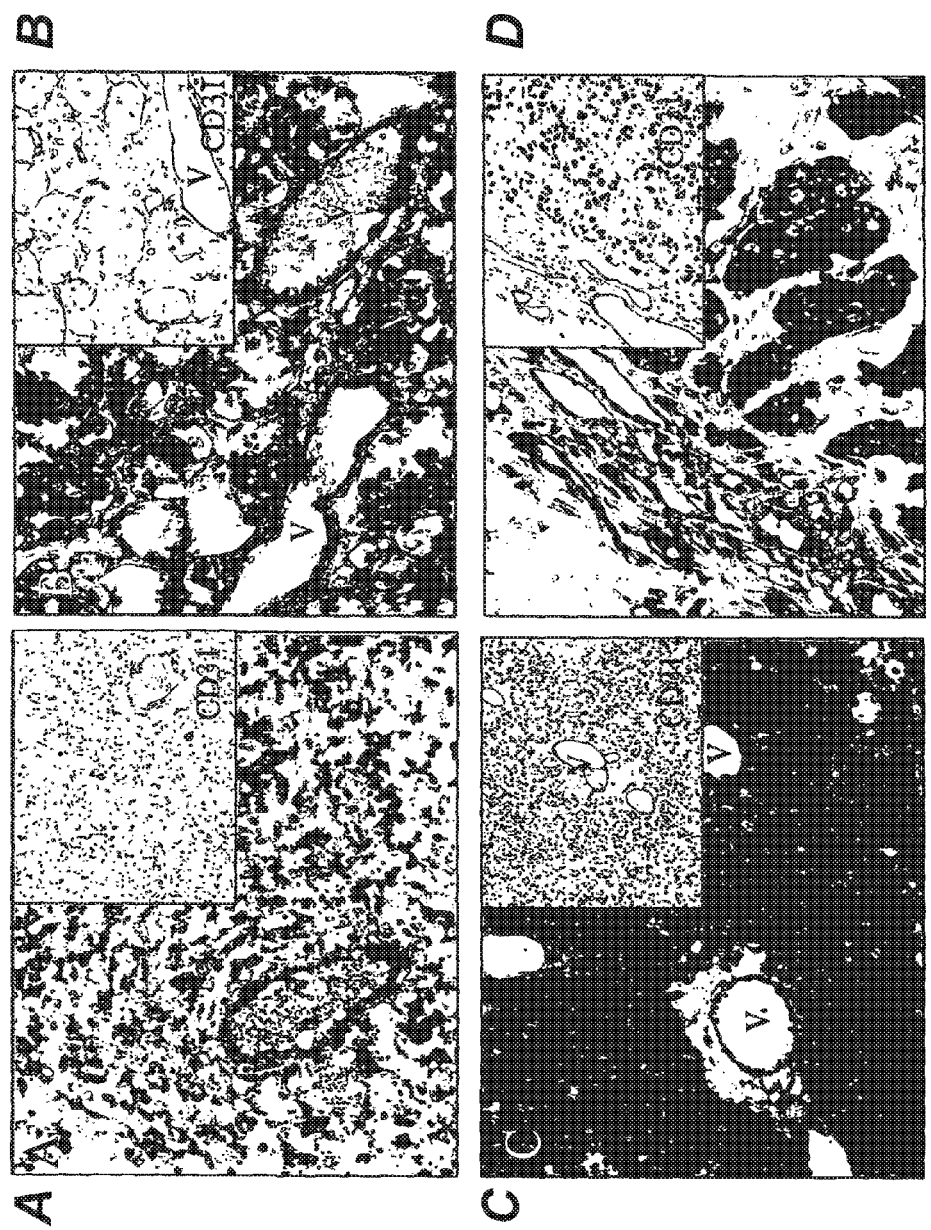
FIG. 3: Human PLXND1-specific ISH analyses of glioblastoma multiforme (Panel A), brain metastases of sarcoma (Panel B), melanoma (Panel C) and mammacarcinoma (Panel D). Insets show CD31 stainings of serial sections. Control ISH using sense probes were negative (not shown). Note that in these tumors, PLXND1 expression is not confined to the blood vessels. Also, in tumor cells, high levels of the PLXND1 transcript are found. t=tumor, V=vessel.
Figure 4:
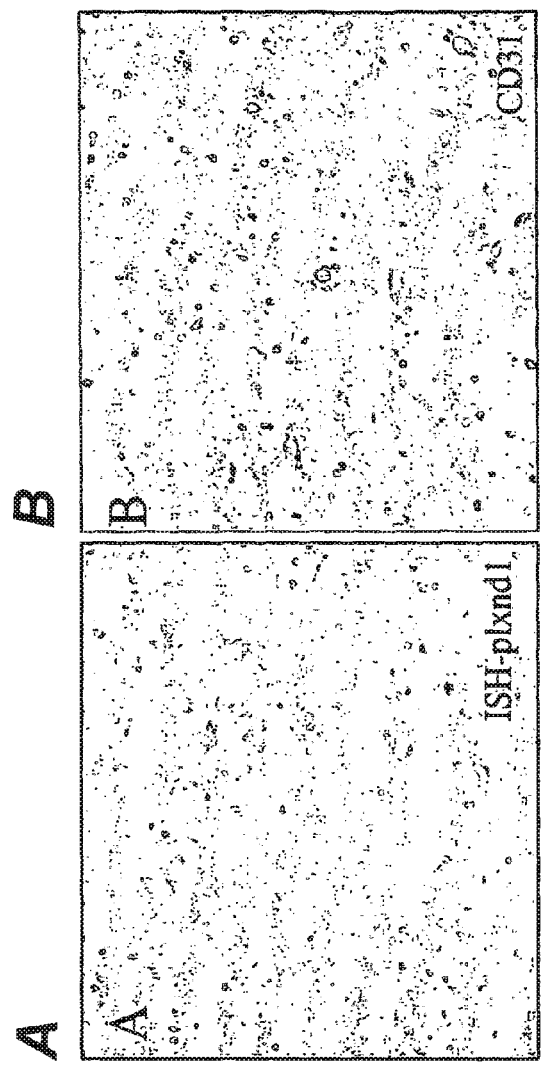
FIG. 4: ISH analysis using a human-specific digoxigenin-labeled RNA probe (Panel A) and immunohistochemical staining with CD31 (Panel B) of normal brain. Note that vessels are abundantly present but these do not express the plexin D1 transcript.

To investigate plexin D1 RNA expression in human tumor samples, in situ hybridizations were performed with a human-specific plexin D1 RNA probe. High plexin D1 RNA expression levels were found in a number of human tumors, including glioblastoma multiforme, brain metastases of sarcoma, renal cell carcinoma, adenocarcinoma of the colon and of the breast, both in tumor vasculature and tumor cells. A summary of plexin D1-expressing tumor types is given in Table 1. FIG. 3 shows some examples of in situ hybridizations, e.g., a glioblastoma, a brain metastasis of melanoma and a brain metastasis of colon carcinoma. Plexin D1 RNA was found not only on the tumor vasculature, but also excessively on the tumor cells themselves. Importantly as in FIG. 4, Panel A, no plexin D1 RNA expression is observed in normal brain vasculature. In FIG. 4, Panel B, a CD31 staining is shown, demonstrating that abundant vessels are present in these sections.

Example 3

Preparation of Antibodies Against Plexin D1

To detect plexin D1 protein, antibodies were selected with affinity toward plexin D1. To this end, a M13 pHENIX phage library was constructed expressing Llama single-domain V-H antibodies, constructed by RT-PCR from Llama B-lymphocytes as described (S. van Koningsbruggen et al., *J. Immunol. Methods* 279:149-161 (2003)). The population of resulting cDNAs encoding V-H-single-domain antibody (sdab) fragments was ligated into phagemid vector pHENIXHis8VSV (results not shown), resulting in a fusion product with an 8*His-tag and a VSV-G-tag at the C-terminus. After electroporation in *E. coli* TG1 cells, ampicillin-resistant colonies were collected and pooled.

The resulting library had a complexity of $8 \times 10^8$ clones. Eighty percent of plasmids contained full-length sdab insert as determined by PCR analysis and immunological dot-blot-detection of the VSV-G-tag in sdabs (see below). The phage library was propagated as phagemids in *E. coli* TG1 bacteria. Phage particles were rescued by infection with trypsin-sensitive helper phage M13K07 (50). Phages were purified and concentrated from the culture supernatant by precipitation with 20% Polyethyleneglycol/2.5 M NaCl via standard methodology.

To select for phages, displaying antibodies with affinity toward plexin D1, immunotubes (Nunc, Roskilde, Denmark) were coated overnight at 4° C. with 5 µg/ml KLH-conjugated peptide (H$_2$N-ALEIQRRFPSPTPTNC-CONH$_2$ (SEQ ID NO:8), corresponding to amino acids 1-16 of the mature human PLXND1 protein (accession no. AY 116661) in 50 mM NaHCO$_3$ (pH 9.6). Of note, the glutamic acid on position 3 in this peptide is a lysine in the mouse sequence; the remaining amino acids are homologous to mouse plxnd1.

After rigorous washing with PBS/0.05% TWEEN® 20 (PBST), non-specific binding sites were blocked with 5% marvel in PBST (MPBST, 1 hour at room temperature (RT)) and $10^{13}$ phage particles from the library stock were incubated with the immobilized peptide for 90 minutes at RT. After rigorous washing with PBST and PBS, bound phages were eluted by trypsin treatment (10 mg/ml, 30 minutes RT).

After trypsin inactivation with 1% newborn calf serum, the eluate was used to infect log-phase TG1 cells to amplify PLXND1-binding phages and calculate number of binders.

To enrich for binding phages, four rounds of selection were performed. From the second round on, selections were performed against unconjugated peptides, immobilized on DNA-binding plates (Costar) to prevent selection of KLH-binders.

Individual PLXND1-binding phages with PCR-confirmed full-length sdab inserts were tested for specificity toward plexin D1. Wells of DNA-binding plates or immunoplates (Nunc) were coated overnight at 4° C. with PLXND1-peptide or an irrelevant peptide (1 µg/well in PBS/0.5 M NaCl pH 9.0), Bovine serum albumin (1 µg/well in 50 mM NaHCO$_3$ pH 9.6) or human Immunoglobulin G (1 µg/well in 50 mM NaHCO$_3$ pH 9.6). After blocking non-specific binding sites with MPBST, wells were incubated with phages in MPBST for 1 hour at RT and non-bound phages removed by rigorous washing. Bound phages were detected using HRP-conjugated anti-M13 (Amersham Pharmacia Biotech, Piscataway, N.J., USA) and tetramethylbenzidine (TMB; bioMerieux B.V., Netherlands). The reaction was terminated with 2 M H$_2$SO$_4$ and enzymatic activity quantified by measuring absorbance at 450 nm using an ELISA reader.

Figure 5:
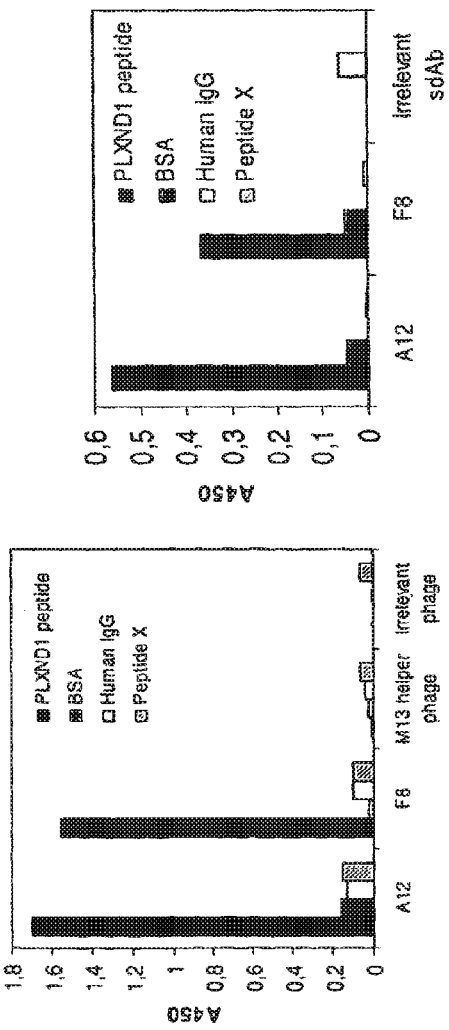
FIG. 5: Specificity of phages (Panel A) and corresponding single-domain antibodies (sdabs) (Panel B) A12 and F8 for peptide $H_2N$-ALEIQRRFPSPTPTNC-$CONH_2$ (SEQ ID NO:8). In Panel A, $10^{10}$ phages were allowed to bind to PLXND1-peptide, BSA, human IgG or irrelevant peptide as described in the text. After rigorous washing, bound phages were detected using an anti-M13 antibody. In Panel B, similar incubations were performed but now with soluble sdabs. After washing, bound sdabs were detected and semi-quantified via the VSV-G-tag.

Using this selection procedure, phages displaying V-H single-domain antibodies A12 and F8 on their surfaces were identified as specific binders. FIG. 5, Panel A, shows that M13 phage-associated antibodies A12 and F8 bind specifically to plexin D1 peptide, but not to bovine serum albumin, immunoglobulins or an irrelevant peptide.

Expression of soluble single-domain antibodies was induced in log-phase *E. coli* TG1 cells by culturing at 30° C. in 2×TYA medium/1 mM IPTG. Sdabs were collected by osmotic lysis using ice-cold TES buffer (200 mM TrisHCl, 0.5 mM EDTA, 500 mM sucrose) containing a protease inhibitor cocktail (Roche, Basel, Switzerland). Sdab concentrations were estimated via dot-blot analysis using the mouse monoclonal anti-VSV-G P5D4, alkaline phosphatase-conjugated rabbit anti-mouse immunoglobulin (Dako, Denmark) and NBT/BCIP staining. Sdabs were tested in ELISA for PLXND1-peptide specificity. Single-domain antibodies A12 and F8 did not bind to irrelevant peptide, not to bovine serum albumin, and not to human immunoglobin G (FIG. 5, Panel B). The dissociation constants (Kds) of the binding between single-domain antibodies A12 and F8 were determined using the Biacore 2000 (Uppsala, Sweden) biosensor. The sensor chip and protein coupling chemicals were purchased from Biacore AB. PLXND1-peptide-KLH conjugate (27 µg/ml in Na-Acetate, pH 4.0) or BSA (1 µg/ml in Na-Acetate, pH 5.0) was coupled to activated CM5 surfaces using N-ethyl-N'-(dimethylaminopropyl) carbodiimide, N-hydroxysuccinimide, under conditions recommended by the manufacturer. Unreacted groups were inactivated by 1 M ethanolamine, pH 8.5.

Kinetic measurements were performed at 25° C. with a flow rate of 10 ml/minute in HBS-EP buffer (10 mM Hepes, pH 7.4, 150 mM NaCl, 3 mM EDTA, 0.005% surfactant P20).

Six concentrations of Ni-affinity-purified sdabs (in the range of 1 mM to 50 µM) were used to determine the dissociation constants (Kds) of the interaction with the PLXND1-peptide. After each experiment, regeneration of the sensor surface was performed with 10 mM NaOH. Specific binding, defined by binding to a PLXND1-surface minus binding to a control BSA-surface, was analyzed using the BIAevaluation 4.1 software and a 1:1 *Langmuir* binding model.

Figure 6:
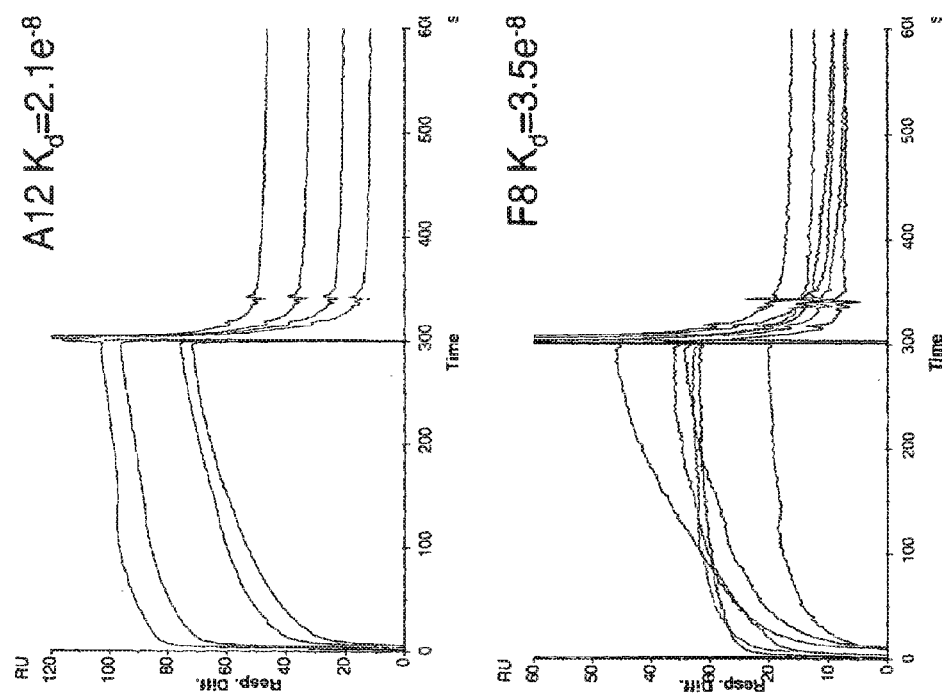
FIG. 6: The dissociation constants (Kds) of the binding between single-domain antibodies A12 and F8 were determined using the Biacore 2000 (Uppsala, Sweden) biosensor. The sensor chip and protein coupling chemicals were purchased from Biacore AB. PLXND1-peptide-KLH conjugate (27 µg/ml in Na-Acetate, pH 4.0) or BSA (1 µg/ml in Na-Acetate, pH 5.0) was coupled to activated CM5 surfaces using N-ethyl-N'-(dimethylaminopropyl)carbodiimide, N-hydroxysuccinimide, under conditions recommended by the manufacturer. Unreacted groups were inactivated by 1 M ethanolamine, pH 8.5.

Affinities of single-domain antibodies A12 and F8 were $2.1 \times 10^{-8}$ M and $3.5 \times 10^{-8}$ M, respectively (FIG. 6).

Example 4

Immunohistochemical Stainings with Single-Domain Antibodies A12 and F8

The single-domain antibodies are tagged at the carboxy-terminal end with a VSV-His-tag, enabling immunohistochemical stainings using an anti-VSV antibody. The following protocol was followed for immunohistochemical stainings with single-domain antibodies A12 and F8. Following deparaffinization, endogenous peroxidase activity was blocked by incubation with 0.03% H$_2$O$_2$. Antigen retrieval was performed by treatment with pronase according to standard protocols. Subsequently, slides were pre-incubated with normal horse or goat serum (to block non-specific binding sites in sections of human and mouse tissues, respectively), followed by incubation with sdabs for 1 hour. Sdabs were detected by sequential 1-hour incubations with a mouse or rabbit anti-VSV-G antiserum (Sigma-Aldrich Chemie B.V., Zwijndrecht, The Netherlands), biotinylated anti-mouse or anti-rabbit antibody as appropriate (Vector, Burlingame, Calif.), and avidin-biotin peroxidase complex (Vector, Burlingame, Calif.). Finally, peroxidase was visualized by the 3-amino-9-ethylcarbazole (ScyTek, Utah, USA) peroxidase reaction with hematoxylin as counterstain. All steps were performed at RT.

The specificity of the antibody A12 and F8 for plexin D1 in immunohistochemical stainings was first examined by staining mouse embryos in which expression patterns of plexin D1 on the RNA level were well characterized (Van der Zwaag et al. (2002), supra), and comparing profiles with immunostainings with anti-endothelial antibody anti-CD31 (DAKO, Glostrup, Denmark). In growth plate of trabecular bone of mice embryos at E16.5, immunostaining was observed on CD31-positive blood vessels. The staining profile correlated well to in situ hybridization for the plexin D1 transcript (FIG. 7, Panel A). The blood vessel origin of PLXND1 expression was further confirmed by performing stainings on serial sections with sdabs and anti-human anti-CD31 antibody (anti-human CD31).

Example 5

Staining of Tumor Cells with F8

Four μm sections cerebral mouse xenografts of the human melanoma cell line Me157-VEGF-A (Kusters et al. (2003), supra) were stained with single-domain antibody F8, according to the protocol exemplified in Example 4. The antibody clearly recognized plexin D1 on tumor blood vessels (FIG. 7, Panel B). To further investigate plexin D1 protein expression on tumors, archival paraffin-embedded or tumor tissue of different origin (glioblastoma multiforme (FIG. 8, Panel A), brain metastases of melanoma (FIG. 8, Panel B) colon carcinoma (FIG. 8, Panel C) and renal cell carcinoma (FIG. 8, Panel D) were immunostained with anti-PLXND1 sdabs. Immunohistochemistry using antibody A12 and comparison with anti-human CD31 stainings on serial sections, showed expression on all tumors examined and confirmed plexin D1 expression on the protein level in tumor cells and in tumor blood vessels.

Example 6

Timing of Plexin Expression on Malignant Cells

To investigate whether expression of plexin D1 occurs on premalignant cells, a progression series of melanoma was stained, consisting of benign nevi, dysplastic nevi, radial growth phase melanoma, invasive melanoma and disseminated melanoma. Melanocytes in benign nevi and dysplastic nevi do not express the protein, whereas malignantly transformed cells, both in radial growth phase and vertical growth phase tumors are positive for the protein (FIG. 9 and Table 2).

Example 7

Activation State of Plexin D1-Expressing Cells

Plexin D1 expression is related to the activation state of the endothelial cells in tumor blood vessels. Treatment with ZD6474, an inhibitor of VEGFR2 and EGFR, was previously shown to block angiogenesis in a mouse brain tumor model, resulting in a phenotypic shift from an angiogenic to a non-angiogenic vessel co-opting phenotype (43). Treatment with ZD6474 resulted in a decrease of plexin D1 expression on tumor-associated blood vessels in a dose-dependent manner (FIG. 10). Thus, plexin D1 expression is a characteristic of activated endothelial cells.

Example 8

Immunohistochemistry with A12 on Normal Tissues

Expression of plexin D1 in normal brain, heart, skin, kidney, spleen, intestine, and endometrium was examined by immunohistochemistry using antibody A12. Vessels in proliferative myometrium-expressed plexin DL showing that plexin D1 is associated not only with pathological angiogenesis, but also with physiological angiogenesis (not shown).

In some instances, co-immunostainings were performed with the CD68 macrophage marker. These stainings revealed that a subpopulation of macrophages expressed the protein (FIG. 11). Also, fibroblasts in skin and some proliferating intestinal epithelial cells were found to express plexin D1 (not shown).

Example 9

Staining of Macrophages in Inflammatory Diseases

To further examine the involvement of plexin D1 in diseases with prominent macrophage involvement, immunohistochemical stainings were performed on atherosclerotic plaques, multiple sclerosis and rheumatoid arthritis. Macrophages express plexin D1.

Example 10

Access to Plexin D1 in Tumor Vessels Via Intravenous Injection

The expression of plexin D1 protein on tumor blood vessels suggests that plexin D1 is accessible via intravenous injection. To test this, $2 \times 10^5$ stably transfected Me157 cells expressing the VEGF-$A_{165}$ isoform were microsurgically injected into the right internal carotid artery of BALB/C nude mice. After 18 days, when animals showed neurological symptoms (Kusters et al. (2003), supra), $10^{12}$ PLXND/-binding phages of clones A12, F8 or non-relevant phages were injected in the tail vein of nude mice, carrying established Me157-VEGF-$A_{165}$ brain metastases (n=2 for A12, n=4 for F8, n=3 for control phage).

In two other groups of mice, 30 μg sdab F8 or a control sdab (n=2 for each group) was intravenously injected. After 5 minutes, mice were anesthetized using isoflurane, the chests were opened, and non-bound phages were washed from the system by cardiac perfusion with 15 ml of phosphate-buffered saline (PBS). Then, mice were sacrificed by cervical dislocation, and parts of brains, hearts, lungs, livers, spleens and kidneys were snap frozen in liquid nitrogen.

Other parts were fixed in formalin to be paraffin-embedded. After short hematoxylin staining, tumors were dissected from 10 μm brain sections using laser capture dissection microscopy (Leica laser dissection microscope). Equivalent areas were dissected from unaffected brain, contralateral to the tumor.

Subsequently, phages were eluted from dissected tissue samples using trypsin treatment and used to infect TG1 cells. Numbers of colony-forming phages were counted and used as a measure of tumor homing. To qualitatively assess tumor homing by phages or sdabs, 4 μm sections, serial to the sections used for laser dissection, were stained with anti-M13 p8 antibody (Abcam Limited, Cambridge, UK) to detect bound phages, or anti-VSV-G antibodies (Sigma-Aldrich) to detect single-domain antibodies.

Intravenous injection of M13 phages displaying anti-PLXND1 single-domain antibody F8, but not phages carrying irrelevant single-domain antibodies, in mice carrying angiogenic melanoma lesions resulted in accumulation of phages in tumor vessels but not to detectable specific presence of phages in normal brain vessels, nor blood vessels in liver, spleen, kidney (FIG. 12, Panels A and D, not shown). This indicates that plexin D1 is expressed at the luminal side of the endothelial cell specifically in tumor blood vessels and thus can be used as a targetable marker.

Injection of the partially purified single-domain antibody accordingly led to preferential tumor localization (FIG. 12, Panel C). In the latter situation, it must be considered that the small molecular weight of 20 kDa of the single-domain antibodies enable extravasation from the highly permeable tumor vessels and accumulation in the tumor interstitium. This latter effect is non-specific and is also observed with non-relevant single-domain antibodies. It is envisioned that antibodies of small molecular weight and relatively low affinities have higher penetrability through tumors and are more suitable for targeting the tumor cell compartment.

Example 11

Accumulation of F8 in Tumor Blood Vessels

Mice were injected transcranially with E98, a glioma xenograft line. E98 tumors are maintained as subcutaneous tumors. A Balbc/c nu/nu athymic mouse carrying a subcutaneous E98 tumor was killed and the tumor removed. The tumor was minced with a sterile scalpel and the homogenate was passed through a sterile 70 μm mesh nylon filter. Twenty μl of the resulting cell suspension, containing 150,000 cells, was injected transcranially in the brain of nude mice. After 3 weeks, M13 phages displaying single-domain antibody F8 were injected intravenously, and after five minutes the mouse was subjected to cardiac perfusion with 15 ml of phosphate-buffered saline.

The mice were killed, brains removed and fixed in formalin. Four μm sections were subjected to immunohistochemistry with anti-M13 antibody, and serial sections were stained immunohistochemically with antibodies against CD34 (endothelial marker) and glut-1 (a marker for pre-existent brain endothelial cells (B. Kusters et al., *Cancer Res.* 62:341-345 (2002)).

Phages carrying anti-plexin D1 single-domain antibodies accumulated specifically in tumor-associated blood vessels, but not in normal vessels (FIG. 13). Importantly, phages also accumulated in tumor blood vessels that were positive for glut-1, and that, therefore, can be considered as pre-existent blood vessels, rather than newly formed blood vessels. This indicates that not only angiogenic blood vessels are subject to targeting with anti-plexin D1 antibodies, but also non-angiogenic, yet activated blood vessels in tumors.

Example 12

Recombinant Plexin D1 Ectodomains Inhibit Angiogenesis

Human melanoma Me157 cells were transfected with the VEGF-$A_{165}$ coding sequence in vector pIREShyg. Stably transfected cells were selected by culturing in 200 μg/ml hygromycin in Dulbecco's Modified Eagle medium (DMEM) supplemented with 10% fetal calf serum (FCS) and penicillin/streptomycin. Because expression of the hygromycin resistance gene is linked to that of the VEGF-A cDNA via the internal ribosomal entry site (IRES), all hygromycin-resistant cells will produce the VEGF-A protein also. Stably transfected Me157-VEGF cells were subsequently transfected with pIRESneo-PlexinD1 ED. The vector contains the cDNA encoding the extracellular domain from nucleotides 1-2745, linked via the IRES to expression of the neomycin resistance gene.

Double transfectants were injected in the right carotid artery of nude mice, and tumors were allowed to develop. At the onset of neurological symptoms (approximately 18 days) mice were subjected to Gadolinium-DTPA-enhanced magnetic resonance imaging. Subsequently, mice were sacrificed, brains fixed in formalin and subjected to immunohistochemical stainings to examine the tumor vasculature.

When compared to controls, consisting of tumors expressing VEGF-A only, Gd-DTPA enhancement in T1-weighted magnetic resonance imaging (MRI) was less (compare FIG. 14, Panel A, representing two examples of Me157-VEGF-$A_{165}$ tumors, with Panel B representing two examples of Me157-VEGF-$A_{165}$/PLEXIND1-ED tumors. In the tumors expressing VEGF-$A_{165}$ and Plexin D1 ectodomain, vasculature shows upregulation of the endothelial marker CD34 (a hallmark of endothelial activation by VEGF-$A_{165}$). The vasculature in tumors expressing VEGF-$A_{165}$ only is negative for the brain endothelial cell marker glut-1, which is consistent with the fact that these vessels are newly made and, therefore, lack brain-endothelial cell-specific markers. As can be seen in FIG. 12, Panel B, the vessels that are associated with tumors that express the plexin D1 ectodomain too, do express glut-1. This is a strong indication that these vessels are actually pre-existent. Thus, the plexin D1 ectodomain does not prevent activation of endothelial cells by VEGF-$A_{165}$, but it does prevent the formation of neovasculature.

Example 13

High-Affinity Antibodies Against Plexin D1

A protein sequence, corresponding to amino acids 47-506 (the 459 most amino terminal amino acids of the mature protein), was expressed in *E. coli* M15 pREP4 cells, using the expression vecor pQE16 (Qiagen). The recombinant protein, which was produced in the bacterial cells as inclusion bodies, was dissolved in denaturing buffer, containing 4 M urea and 1 mM dithiothreitol (DTT) and afterwards gradually dialyzed against PBS. The protein was used to immunize BALB c/c mouse 25 according to standard procedures.

FIG. 15 shows the characteristics of the mouse serum. As shown in FIG. 15, Panel B, the mouse immune serum specifically recognized *E. coli* recombinant protein 47-506 (52 kDa, lane 1), and a second recombinant plexin D1 sequence of 18 kDa, comprising amino acids 225-388 (thus lying completely within the sequence that was used for immunization, lane 2). The pre-immune serum did not show such a reactivity (Panel A).

When tested in immunohistochemical stainings on a brain metastasis of an alveolar soft tissue sarcoma, the mouse immune serum (Panel D), but not the pre-immune serum (Panel C), showed positivity toward blood vessels and tumor cells, a staining pattern that was similar to that of single-domain antibody A12. Thus, the B-lymphocytes of this mouse were considered suitable to generate hybridomas of spleen B-lymphocytes with myeloma cell line SP2/0.

From these hybridomas, a number of antibody-producing cell lines were selected based on reactivity against protein 47-506 in ELISA, and were analyzed for their potential to detect plexin D1 in frozen sections of human tumors. Of these, 11F5H6 and 17E9C12, both antibodies of the IgM subtype, showed strong positivity in brain metastases of sarcoma and melanoma, as illustrated in FIG. 16. The insets in Panels C-F represent control stainings in which the primary antibody was omitted. Panels A and B show that these antibodies do not notably recognize vessel structures in normal brain tissue.

Example 14

Monoclonal Antibody 11F5H6 is Able to Recognize Tumor Blood Vessels

To further evaluate whether monoclonal antibody 11F5H6 is able to recognize tumor blood vessels, angiogenic Me157-VEGF-A tumors were grown in brains of nude mice, essentially as described in Example 10. Antibody 11F5H6 (1 mg) was injected in a lateral tail vein and allowed to circulate for 15 minutes. After this period, the mice were anesthetized with 1.3% isoflurane and the chest was opened, upon which a cardiac perfusion was performed with 20 ml phosphate-buffered saline.

After this procedure, mice were decapitated, and brains removed and snap-frozen or fixed in formalin. Frozen sections of 4 μm were stained with anti-IgM antibody. In FIG. 17, Panel A, it is shown that antibody 11F5H6 homes to and accumulates in tumor vessels but not in normal vessels (compare anti-IgM staining in FIG. 17, Panel A, with the anti-endothelial CD31 staining in FIG. 17, Panel B). Such staining is not seen when performing anti-IgM staining on non-injected mice. Thus, 11F5H6 is a promising antibody that allows tumor targeting.

Example 15

Plexin D1 Expression in Rheumatoid Arthritis

Plexin D1 is expressed in macrophages in mouse models of rheumatoid arthritis (FIG. 18). A subset of macrophages in human atherosclerotic plaques also expresses plexin D1 (FIG. 19). Stainings were performed with single-domain antibody A12. In FIG. 19, a double staining was performed, displaying plexin D1 in red and the macrophage marker CD68 in blue. A purple color indicates co-expression.

```
Sequences
A12 (SEQ ID NO: 1):
ATGAAATACCTATTGCCTACGGCAGCCGCTGGATTGTTATTACTCGCG

GCCCAGCCGGCCATGGCCCAGGTGCAGCTGCAGGAGTCTGGGGGAGGCTT

GGTGCAGCCTGGGGGGTCTCTGAGACTCTCCTGTGCAGCCTCTGGAAGCA

GTATCAGTATCAATAACTGGGGCTGGTACCGCCAGGCTCCAGGAAAACAG

CGCGAGCGGGTCGCAGCTATATCTGGTGGTGGTAAAACAGTCTATGCGGA

CTCCGTGAAGGGCCGATTCACCATCTCCAGAGACAACGCCAAGAACACGG

TGTATCTGCAAATGAACAGCCTGAAACCTGAGGATACGGCCGTCTATTAC

TGTAGAGCAGTCCGGAAAAGTACGGGTTGGCTTAGGGGGCTTGACGTCTG

GGGCCAGGGGACCCAGGTCACCGTCTCCGCAGAACCCAAGACACCAAAAC

CACAACCAGCGGCCGCACATCATCACCATCATCACCATCATTATACAGAC

ATAGAGATGAACCGACTTGGAAAGGGGGCCGCATAG

A12 protein sequence (SEQ ID NO: 2)
MKYLLPTAAAGLLLLAAQPAMAQVQLQESGGGLVQPGGSLRLSCAASG

SSISINNWGWYRQAPGKQRERVAAISGGGKTVYADSVKGRFTISRDNAKN

TVYLQMNSLKPEDTAVYYCRAVRKSTGWLRGLDVWGQGTQVTVSAEPKTP

KPQPAAAHHHHHHHYTDIEMNRLGKGAA@

F8 (SEQ ID NO: 3):
ATGAAATACCTATTGCCTACGGCAGCCGCTGGATTGTTATTACTCGCG

GCCCAGCCGGCCATGGCCCAGGTGCAGCTGCAGGAGTCTGGGGGAGGATT

GGTGCAGGCTGGAGACTCTCTGAGACTCTCCTGTGCAGCCTCTGGACGCA

CCTTCAGTACTTTGATTATGGCCTGGTTCCGCCAGGCTCCAGGGAAGGAG

CGTGAATTTGTAGCGGCGATTAGCCGGGGTGGCGGTAGCACAAGCTATGC

AGACTCCGTGAAGGGCCGATTCACCATCTCCAGAGACAATTCCAAGAACG

CGGTGTATCTACAAATGAACAGCCTGAAACCTGATGACACGGCCGTCTAT

TACTGTAATGCCCGGTACGGTAGCCGAATTTACTGGGGCCAGGGGACCCA

GGTCACCGTCTCCTCAGAACCCAAGACACCAAAACCACAACCAGCGGCCG

CACATCATCACCATCATCACCATCATTATACAGACATAGAGATGAACCGA

CTTGGAAAGGGGGCCGCATAG

F8 protein sequence (SEQ ID NO: 4)
MKYLLPTAAAGLLLLAAQPAMAQVQLQESGGGLVQAGDSLRLSCAASG

RTFSTLIMAWFRQAPGKEREFVAAISRGGGSTSYADSVKGRFTISRDNSK

NAVYLQMNSLKPDDTAVYYCNARYGSRIYWGQGTQVTVSSEPKTPKPQPA

AAHHHHHHHYTDIEMNRLGKGAA@

Sequence single chain antibody, derived from
antibody 11F5H6 (SEQ ID NO: 5)
MKYLLPTAAAGLLLLAAQPAMADYKDIVMTQTPLSLPVSLGDQASISCR

SSQSIVHSNGNTYLEWYLQKPGQSPKLLIYKVFNRLSGVPDRFSGSGSGT

DFTLKISRVEAEDLGVYYCFQGSHVPLTFGAGTKLELKRGGGGSGGGGSG

GGGRAPGGGGSEVQLQQSGPELVKPGASMKISCKASGYSFTGYTMNWVKQ

SHGKNLEWIGLINPYNGGTSYNQKFKGKATLTVDKSSSTAYMELLSLTSE

DSAVYYCARAITTDGWFAYWGQGTLVTVSAAAAHHHHHHHYTDIEMNRL

GKGAA

Sequence single chain antibody, derived from
antibody 17E9C12 (SEQ ID NO: 6)
MKYLLPTAAAGLLLLAAQPAMADYKDIQMTQTPSSLAVSAGEKVTMSC

KSSQSVLYSSNQKNYLAWYQQKPGQSPKLLIYWASTRESGVPDRFTGSGS

GTDFTLTISSVQAEDLAVYYCHQYLSSWTFGGGTKLEIKRGGGGSGGGGS

GGGGSGGGGSQVQLQQSGAELVKPGASVKLSCTASGFNIKDTYMHWVKQR

PEQGLEWIGRIDPANGNTKYDPKFQGKATITADTSSNTAYLQLSSLTSED

TAVYYCAMDYWGQGTSVTVSSAAAHHHHHHHYTDIEMNRLGKGAA
```

TABLE 1

PLXND1 expression in human tissues

| Tissue | PLXND1 expression |
|---|---|
| Malignant | |
| Adenocarcinoma of oesophagus (n = 1) | Tumor vessels and tumor cells |
| Adenocarcinoma of rectum (n = 5) | Tumor vessels, tumor cells and macrophages |
| Adenocarcinoma of prostate (n = 1) | Tumor vessels and tumor cells |
| Alveolar soft part sarcoma of femur (n = 1) | Tumor vessels and tumor cells |
| Astrocytoma (n = 1) | Tumor vessels |
| Carcinoid tumor of lung (n = 1) | Tumor vessels, tumor cells and macrophages |
| Ductal carcinoma in situ of mamma (n = 5) | Tumor vessel, tumor cells, macrophages, fibroblasts |
| Follicular lymphoma (n = 8) | Tumor vessels |
| Glioblastoma Multiforme (n = 3) | Tumor vessels and tumor cells |
| Brain metastasis of adenocarcinoma (n = 4) (mamma, lung, rectum) | Tumor vessels and tumor cells |
| Brain metastasis of alveolar soft part sarcoma (n = 1) | Tumor vessels and tumor cells |
| Brain metastasis of renal cell carcinoma (n = 1) | Tumor vessels and tumor cells |
| Liver metastasis of adenocarcinoma colon (n = 2) | Tumor vessels, tumor cells and macrophages |
| Lobular carcinoma in situ of mamma (n = 3) | Tumor vessels and tumor cells weakly positive, macrophages and fibroblasts |
| Lymph node metastasis ductal mamma carcinoma (n = 1) | Tumor cells and some tumor vessels |
| Ovary metastasis of adenocarcinoma colon (n = 1) | Tumor cells and myofibroblasts |
| Renal cell carcinoma (n = 1) | Tumor vasculature and tumor cells |
| Urothelial cell carcinoma of prostate (n = 2) | Tumor vessel, tumor cells and macrophages |
| Non-malignant | |
| Bladder (n = 1) | Macrophages |
| Blood vessel, atherosclerosis (n = 6) | Macrophages |
| Bone marrow (n = 2) | |
| Brain cortex (n = 1) | Some neurons perinuclear |
| Brain. Alzheimer + CAA (n = 1) | |
| Endometrium | |
| Proliferation phase (n = 5) | Macrophages |
| Secretion phase (n = 4) | Macrophages |
| Secretion/menstruation phase (n = 1) | Macrophages |
| Endometriosis interna (n = 1) | Macrophages |
| Heart (n = 1) | Some muscle cells perinuclear |
| Large intestine (n = 1) | Some luminal staining of epithelium, macrophages, fibroblasts |
| Liver (n = 1) | Liver cells perinuclear granular, macrophages |
| Lung (n = 2) | Macrophages |
| Mamma (n = 2) | Some epithelial cells perinuclear |
| Mamma, ductal hyperplasia (n = 1) | Focal epithelial cells perinuclear, macrophages |
| Oesophagus (n = 1) | Macrophages |
| Small intestine (n = 1) | Some luminal staining of epithelium, macrophages, fibroblasts |
| Spleen (n = 1) | Macrophages |

TABLE 2

PLXND1 expression in melanoma progression series

| | Absent | Moderate | Abundant |
|---|---|---|---|
| Naevocellular naevi (n = 18) | 18 | | |
| Atypical naevi (n = 14) | 14 | | |
| Melanomas in situ (n = 5) | 5 | | |
| Primary melanomas (n = 26) | 4 | 2 | 20 |
| Melanoma metastases | | | |
| Lymph node (n = 9) | 1 | 2 | 6 |
| Skin (n = 5) | 1 | 1 | 3 |
| Brain (n = 5) | | | 5 |
| Lung (n = 1) | | | 1 |

What is claimed is:

1. A method for treating a subject having a cancer mediated by expression of plexin D1, the method comprising:
    administering to the subject an antibody or an antibody fragment that binds to plexin D1;
    wherein the cancer is selected from the group consisting of hemangioblastoma, prostate carcinoma, renal cell carcinoma, renal clear cell carcinoma, squamous cell carcinoma, melanoma, lung carcinoma, small-cell lung carcinoma, non-small-cell lung carcinoma, and soft tissue sarcoma; and
    wherein the antibody or antibody fragment that binds to plexin D1 is conjugated to an effector compound.

2. The method according to claim 1, wherein the effector compound is selected from the group consisting of a toxin, a thrombosis-inducing compound, a chemotherapeutic agent, a radioactive moiety, an apoptosis-inducing peptide, a peptide comprising the peptide KLAKLAKKLAKLAK (SEQ ID NO:7), a nanodevice, a liposome, a polymersome, a polymersome composed of block copolymers, a truncated tissue factor, doxorubicin, cisplatin, bleomycin sulfate, carmustine, chlorambucil, cyclophosphamide hydroxyurea, technetium 99m, iodine-123, iodine-131, rhenium-186 or -188, gallium-67, yttrium-90, and lutetium-177.

3. The method according to claim 1, wherein the effector compound is a toxin.

* * * * *